United States Patent
Masumura

(10) Patent No.: US 10,760,956 B2
(45) Date of Patent: Sep. 1, 2020

(54) WAVEFRONT CONTROL APPARATUS, WAVEFRONT CONTROL METHOD, INFORMATION ACQUIRING APPARATUS, AND STORAGE MEDIUM

(71) Applicant: CANON KABUSHIKI KAISHA, Tokyo (JP)

(72) Inventor: Takahiro Masumura, Utsunomiya (JP)

(73) Assignee: CANON KABUSHIKI KAISHA, Tokyo (JP)

(*) Notice: Subject to any disclaimer, the term of this patent is extended or adjusted under 35 U.S.C. 154(b) by 256 days.

(21) Appl. No.: 15/635,682

(22) Filed: Jun. 28, 2017

(65) Prior Publication Data

US 2018/0010961 A1   Jan. 11, 2018

(30) Foreign Application Priority Data

Jul. 5, 2016  (JP) .................. 2016-133424
Jun. 8, 2017  (JP) .................. 2017-113432

(51) Int. Cl.
   *G01J 1/32*  (2006.01)
   *G01J 1/08*  (2006.01)
   *A61B 5/00*  (2006.01)

(52) U.S. Cl.
   CPC ............. *G01J 1/08* (2013.01); *A61B 5/0095* (2013.01); *A61B 5/0066* (2013.01); *A61B 5/0068* (2013.01); *A61B 5/0075* (2013.01)

(58) Field of Classification Search
   CPC ........ G01J 1/08; A61B 5/0066; A61B 5/0068; A61B 5/0075; A61B 5/0095
   USPC ....................................................... 250/205
   See application file for complete search history.

(56) References Cited

U.S. PATENT DOCUMENTS

| 7,046,365 B1* | 5/2006 | Aoshima | .................. G01J 11/00 356/450 |
| 8,629,413 B2 | 1/2014 | Betzig et al. | |
| 2008/0285602 A1* | 11/2008 | Nagai | ..................... H01S 3/134 372/20 |

(Continued)

FOREIGN PATENT DOCUMENTS

| WO | 2012068394 A1 | 5/2012 |
| WO | 2013010151 A1 | 1/2013 |

OTHER PUBLICATIONS

Vellekoop et al. "Demixing light paths inside disordered metamaterials." Optics Express. Jan. 7, 2008:67-80. vol. 16, No. 1. Cited in Specification.

(Continued)

*Primary Examiner* — Georgia Y Epps
*Assistant Examiner* — Kevin Wyatt
(74) *Attorney, Agent, or Firm* — Rossi, Kimms & McDowell LLP

(57) ABSTRACT

A wavefront control apparatus includes a detector configured to detect a signal generated from a medium onto which light is irradiated, and a controller configured to control a wavefront of the light based on an output of the detector. The controller performs first processing for forming a first wavefront of the light based on the signal generated from a first measurement position in the medium, and second processing for forming a second wavefront of the light based on the signal generated from a second measurement position different from the first measurement position in the medium onto which the light having the first wavefront is irradiated.

17 Claims, 9 Drawing Sheets

(56) References Cited

U.S. PATENT DOCUMENTS

| | | | |
|---|---|---|---|
| 2011/0071402 A1 | 3/2011 | Masumura | |
| 2012/0127557 A1* | 5/2012 | Masumura | A61B 5/0095 |
| | | | 359/291 |
| 2013/0342665 A1* | 12/2013 | Wang | H04N 5/30 |
| | | | 348/61 |
| 2014/0009808 A1* | 1/2014 | Wang | G02F 1/33 |
| | | | 359/10 |
| 2016/0124221 A1* | 5/2016 | Huang | G01M 11/0264 |
| | | | 359/239 |

OTHER PUBLICATIONS

Tang et al. "Superpenetration optical microscopy by iterative multiphoton adaptive compensation technique." Proceeding of the National Academy of Sciences USA. 2012:8434-8439. vol. 109(22). Cited in Specification.

Yang et al. "Three-dimensional scanning microscopy through thin turbid media." Optics Express. Jan. 30, 2012:2500-2506. vol. 20, No. 3. Cited in Specification.

Vellekoop et al. "Phase control algorithms for focusing light through turbid media." Optics Communications 281. 2008:3071-3080. Cited in Specification.

Conkey et al. "Genetic algorithm optimization for focusing through turbid media in noisy environments," Optics Express. 2012:4840-4849. vol. 20, No. 5. Cited in Specification.

Bifano et al. "MEMS spatial light modulators for controlled optical transmission through nearly opaque materials." Proc. of SPIE. 2012:82530L-1-82530L-9. vol. 8253. Cited in Specification.

* cited by examiner

WAVEFRONT CONTROL APPARATUS, WAVEFRONT CONTROL METHOD, INFORMATION ACQUIRING APPARATUS, AND STORAGE MEDIUM

BACKGROUND OF THE INVENTION

Field of the Invention

The present invention relates generally to a wavefront control apparatus. The present invention is applicable, for example, to an apparatus configured to measure or image an optical property of a scattering medium using light.

Description of the Related Art

A research has been progressed for imaging an optical property inside a medium, such as a biological tissue, using light from a visible range to a near-infrared range in a noninvasive or low invasive manner. In general, the light propagates in the scattering medium, such as the biological tissue, along an irregular path due to scattering. Thus, the light does not reach a sufficient deep position in the medium where multiple scattering happens, and thus the imaging resolution and the imaging depth (penetration depth) deteriorate. In order to image the scattering medium with a high resolution, it is general to remove the scattered light and to extract only the signal light (non-scattered light or weak scattered light of which number of scattering is very small) as seen in a confocal microscope and OCT (Optical Coherence Tomography). These methods are effective to a relatively shallower imaging area, but in a deeper imaging area, the non-scattered light which is the signal source exponentially decreases since the scattering is dominant. It is thus very difficult to apply these imaging methods to the deeper area in the medium. These imaging methods are generally limited to an area where penetration depth is small (such as 1 mm or less in a living tissue). In another case, when an object is captured in a wide range where fine particles exist in an atmosphere as in a fog, smoke, or haze or where the refractive index spatially fluctuates due to the atmosphere, the captured object image is distorted and the object is hard to recognize.

As a solution for this problem, there has recently been proposed a technology for efficiently sending the light to a specific position inside the scattering medium by properly shaping the wavefront of the light incident onto the medium.

I. M. Vellekoop, E. G. Van Putten, A. Lagendijk and A. P. Mosk, "Demixing light paths inside disordered metamaterials," Optics Express Vol. 16, No. 1, pp. 67-80 (2008) irradiates light onto a scattering medium, monitors fluorescent light generated from a fluorescent material in the medium with a CCD, and shapes an incident wavefront with a SLM (Spatial Light Modulator) so that the fluorescent signal becomes maximum. This prior art demonstrates efficiently focusing of the light into the fluorescent material by repeating the monitoring of the fluorescent signal with the CCD and the shaping of the incident wavefront with the SLM, and by optimizing the incident wavefront so as to maximize the fluorescent signal. U.S. Patent Application Publication No. 2012/0127557 discloses a configuration using a photoacoustic signal for a target of a wavefront optimization, instead of the fluorescent signal. Alternatively, Jianyong Tang, Ronald N. Germain and Meng Cui, "Super-penetration optical microscopy by iterative multiphoton adaptive compensation technique," Proceeding of the National Academy of Sciences USA, 109(22) pp. 8434-8439 (2012) discloses a configuration that sets a fluorescent signal by two photons absorptions (TPF: Two-photon fluorescence) to a target. Thus, the light can be focused inside the scattering medium by setting a variety of signals to an target for an optimization. A signal that can be used as the target for the optimization is different from the multiple scattered light.

As disclosed in U.S. Patent Application Publication No. 2011/0071402, the incident wavefront shaping technology may use phase conjugate light which is different from the iterative optimization processing. U.S. Patent Application Publication No. 2011/0071402 generates an ultrasound focus volume at an arbitrary position inside a scattering medium so as to emit light (ultrasound modulated light) modulated in this area to the outside of the medium, and selectively records the wavefront of the ultrasound modulated light in a hologram. This reference then generates a phase conjugate wavefront based on the hologram, and introduces the phase conjugate wavefront into the medium. Thereby, the phase conjugate light propagates in the ultrasound focus volume according to the time reversibility. This effect can effectively send the light to the ultrasound focus volume in the medium. In addition to the ultrasound modulated light, Xin Yang, Chia-Lung Hsieh, Ye Pu and Demetri Psaltis, "Three-dimensional scanning microscopy through thin turbid media," Optics Express Vol. 20, No. 3, pp. 2500-2506 (2012) discloses a phase conjugate light technology utilizing the SHG (Second Harmonic Generation) generated from a certain position in the medium.

The light focusing technology into the scattering medium is available when the wavefront of the light to be irradiated into the medium is properly shaped (with the iterative optimizations or the phase conjugate light technology) based on a signal different from the scattered light, which is referred to as a target signal or guide star. The signal different from the scattered light is, for example, a fluorescent signal, TPF, SHG, a photoacoustic signal, an ultrasound modulated signal, etc. Several combinations of the light focusing technology into the scattering medium with each of a variety of imaging methods are proposed A combination of the light focusing technology at a specific position in the scattering medium with a variety of measurement methods can efficiently focus the light at the target, enhance the measurement signal, and measure the optical property in the medium. As described above, in order to focus the light at the specific position in the scattering medium, it is necessary to shape or optimize the wavefront of the incident light based on the target signal generated from that position. In other words, without measuring the target signal, none of the iterative optimizations and the phase conjugate light technology is applicable. The light focusing technology is effective as long as a target signal in the medium can be measured from the outside of the medium. When the target is located at the deep position in the medium, the target signal attenuates due to the multiple scattering and it becomes difficult to measure the target signal. Then, none of the iterative optimizations or the phase conjugate technology is applicable. As a consequence, the light cannot be focused at the deeper position in the medium and thus the optical performance at the deeper position in the medium cannot be measured. In other words, the penetration depth of the optical property cannot be improved.

SUMMARY OF THE INVENTION

The present invention provides a wavefront control apparatus, a wavefront control method, an information acquiring apparatus, and a storage medium, which is advantageous to an acquisition of an optical property information at a deep position in a scattering medium or a wide range.

A wavefront control apparatus according to one aspect of the present invention includes a detector configured to detect a signal generated from a medium onto which light is irradiated, and a controller configured to control a wavefront of the light based on an output of the detector. The controller performs first processing for forming a first wavefront of the light based on the signal generated from a first measurement position in the medium, and second processing for forming a second wavefront of the light based on the signal generated from a second measurement position different from the first measurement position in the medium onto which the light having the first wavefront is irradiated.

Further features of the present invention will become apparent from the following description of exemplary embodiments with reference to the attached drawings.

DESCRIPTION OF THE EMBODIMENTS

Referring now to the accompanying drawings, a description will now be given of embodiments of the present invention. In the present invention, the wavefront control apparatus and method are configured to control (or adjust) a wavefront of light irradiated onto a medium. The wavefront control method is implemented by a program executed by a computer that constitute a controller, which will be described later. "S" stands for the step in the figure. An information acquiring apparatus is configured to acquire information of an optical property inside the medium, and can include the wavefront control apparatus. The information acquiring apparatus covers a measurement apparatus configured to measure the optical property in the medium and an imaging apparatus configured to image the optical property in the medium.

First Embodiment

Figure 1:
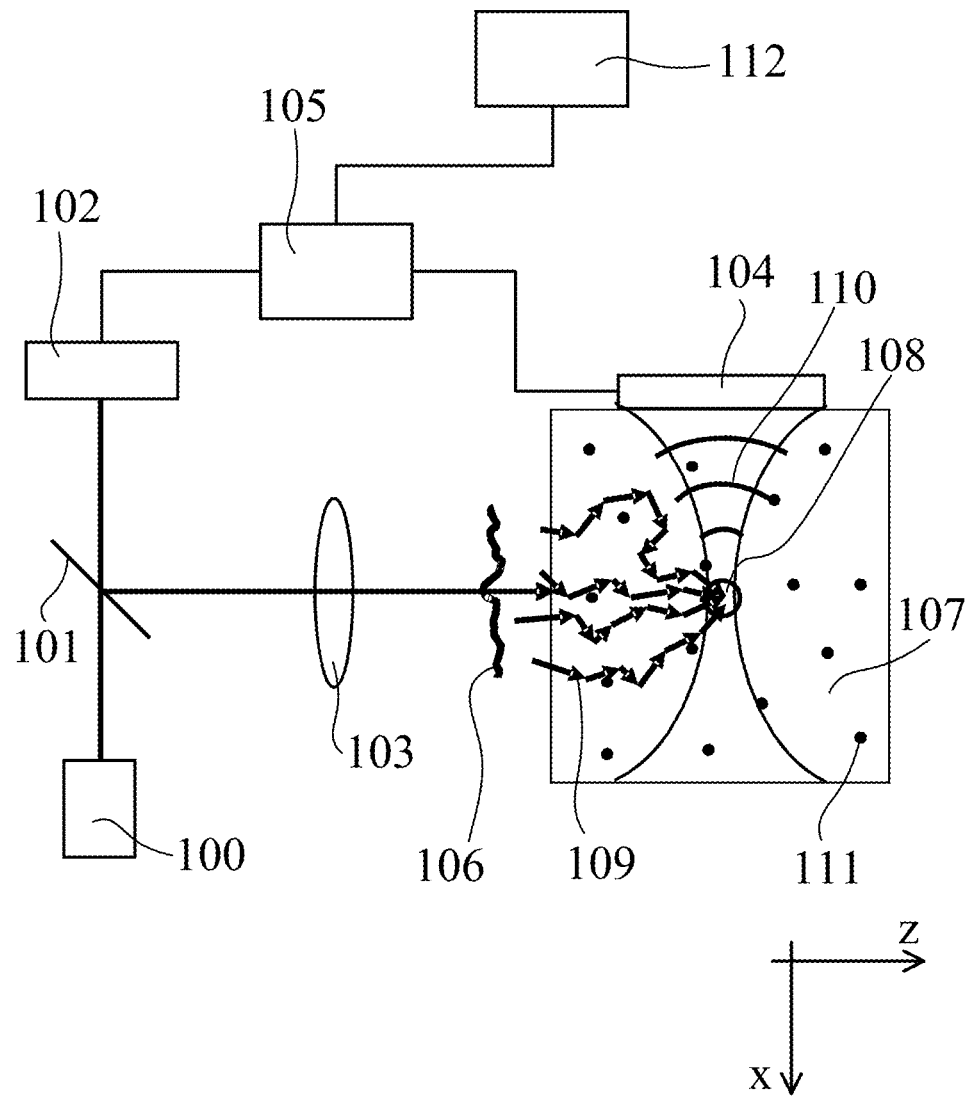
FIG. 1 schematically illustrates a configuration of a measurement apparatus according to a first embodiment of the present invention.

Referring now to FIGS. 1 to 4, a description will be given of a measurement method and a measurement apparatus of an optical property in a scattering medium according to a first embodiment of the present invention. FIG. 1 schematically illustrates an exemplary configuration of the measurement apparatus according to this embodiment. A medium 107 is a test medium that contains a living tissue, or a scattering medium for light from a visible range to a near-infrared range that includes scattering particles 111. A description will now be given of an imaging apparatus according to the present invention using a photoacoustic signal for the medium 107.

A light source 100 emits pulsed light of several nanometers. The light source 100 can select one of a plurality of wavelengths according to an absorption spectrum of an ingredient of a living tissue, such as water, fat, protein, oxyhemoglobin, and deoxyhemoglobin, when the medium 107 is the living tissue. One embodiment uses an electromagnetic wave source configured to emit an electromagnetic wave having a wavelength from the visible range to the near-infrared range, such as 400 nm to 1,500 nm. Similarly, when the medium 107 is the living tissue, the radiated light intensity is adjusted in a safe range.

The light irradiated from the light source 100 transmits a beam splitter 101, and enters an SLM 102. The SLM 102 can be, for example, liquid crystal on silicon (LCOS). The SLM 102 is controlled by a control unit 105 so as to shape a wavefront (or modulate a phase) based on the optimization processing illustrated in FIG. 3. The optimization processing illustrated in FIG. 3 will be described later. The SLM 102 and the control unit 105 constitute a controller configured to control the wavefront of the light based on the output of an ultrasonic transducer, which will be described later. Light 106 that has a shaped wavefront and is reflected on the SLM 102 is reflected on the beam splitter 101 and enters the medium 107 via an optical system 103.

Light 109 that enters the scattering medium 107 propagates inside of the medium 107 while being scattered. When a part of the energy of the light 109 is absorbed by an absorber located at a specific position (area) 108, the temperature rises in the local area, the volume expands, and an acoustic wave (photoacoustic signal) 110 is generated. The ultrasonic transducer 104 serves as a detector (measurement unit) configured to detect or measure the signal generated from the scattering medium 107 onto which the light is irradiated, and to measure the photoacoustic signal 110. The control unit 105 controls focusing of the ultrasonic transducer 104 so as to detect the signal that contains the photoacoustic signal 110 generated from the local area 108 in the scattering medium 107. The ultrasonic transducer 104 includes, for example, a linear array probe, and can generate an ultrasound focus volume at an arbitrary position inside the medium 107 using the electronic focusing using the array probe. The transducer can use a transducer utilizing a piezoelectric phenomenon, a transducer utilizing a light resonance, a transducer utilizing a capacity change, etc. The ultrasonic transducer 104 is sonically matched with the medium 107.

A photoacoustic signal P(z) at a depth z (or a position z) in a medium from the light entrance position is expressed as follows with a light intensity Φ(z) at the position z, an absorption coefficient $\mu_a(z)$ of the absorber at the position z, and a Grueneisen constant Γ representing a conversion efficiency from the heat to the acoustic wave.

$$P(z)=\Gamma\mu_a(z)\Phi(z) \qquad (1)$$

As understood from the expression (1), if the Grueneisen constant Γ and the absorption coefficient $\mu_a(z)$ are peculiar to and constant for the medium at the position z, the photoacoustic signal changes according to the light intensity at the position z. When the light is efficiently focused on the position z, the signal intensity of the photoacoustic signal P(z) enhances.

Figure 2:
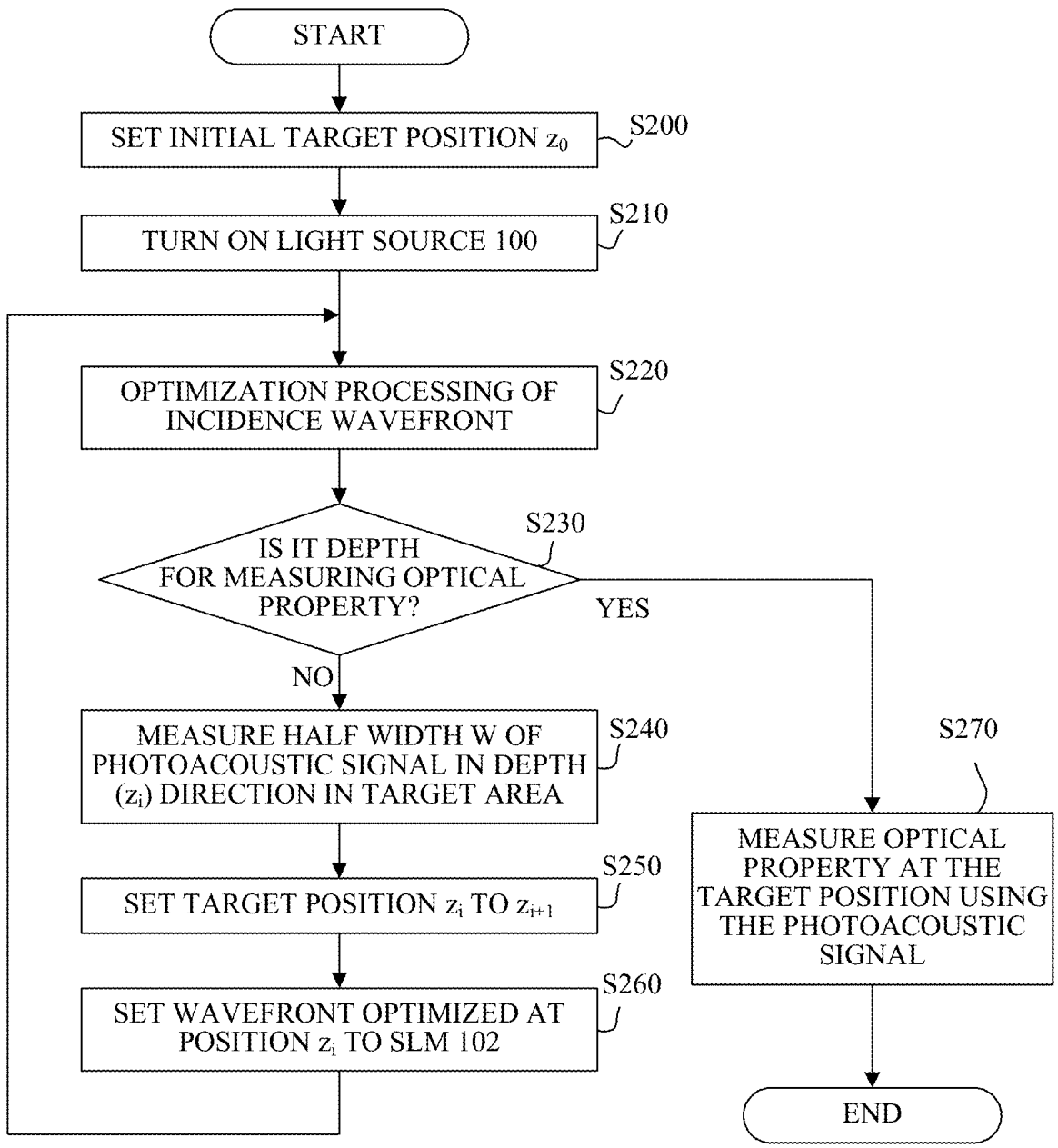
FIG. 2 schematically illustrates an overall processing flow of a measurement method according to the first embodiment of the present invention.
Figure 3:
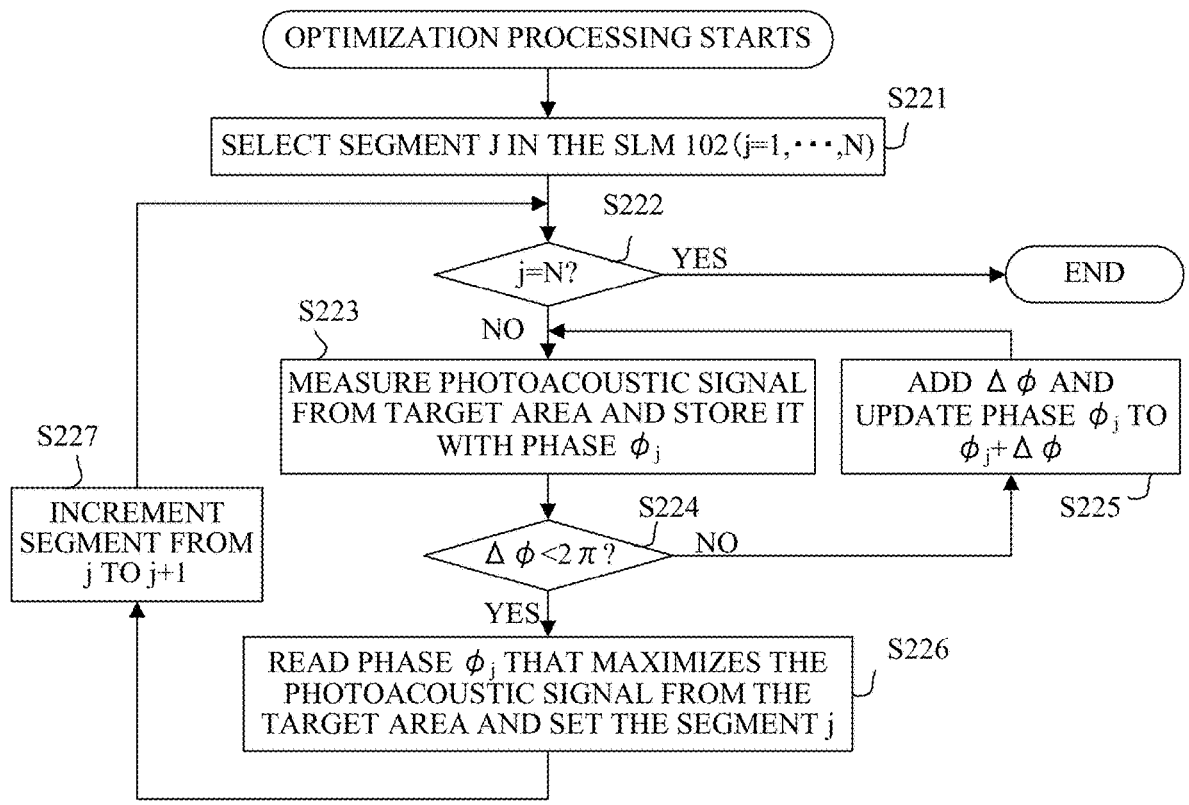
FIG. 3 schematically illustrates optimization processing flow of an incident wavefront according to the first embodiment of the present invention.

The SLM 102 is placed at a pupil plane for the optical system 103, and each segment on the SLM 102 (which is a small area where a phase can be controlled independently) independently shapes the wavefront of the incident light. Referring now to FIGS. 2 and 3, a description will be given of an overall measurement flow of photoacoustic imaging according to this embodiment which includes wavefront shaping or optimization of the incident light.

Initially, the step S200 sets a local target area 108 (target position $z_0$) configured to measure a photoacoustic signal. The depth of the initial target area 108 from the entrance position of the incident light is arbitrarily set as long as the photoacoustic signal can be measured. A proper depth where the signal intensity is sufficiently large to measure may be searched by repeating the measurement a plurality of times.

Next, the step S210 turns on the light source 100. When the ultrasonic transducer 104 starts receiving the photoacoustic signal, the flow moves to the wavefront optimization processing of the incident light in the next step S220. The optimization processing in the step S220 optimizes the wavefront of the incident light so as to maximize the intensity of the photoacoustic signal generated from the target area 108 set in the step S200. As described above, due to the expression (1), the photoacoustic signal enhances if the wavefront is shaped so that the light intensity is focused on the target area 108. The optimization process of the incident wavefront in the step S220 sets the incident wavefront optimized in the last procedure, to the initial state, and executes the step S220 (see the step S260, which will be described later). However, the optimization processing in the step S220 at the initial target position $z_0$ where the step S230 and the subsequent steps have not yet been executed, may set, for example, a plane wave to the initial condition of the optimization.

Referring now to FIG. 3, a description will be given of the optimization processing in the step S220. Initially, the step S221 selects a segment with an index j among N divided segments on the SLM 102. The segment may be one pixel in the SLM 102, or an area that contains a plurality of pixels in the SLM 102.

When the step S223 to the step S227 end for all N segments in the step S222, the optimization processing (S220) ends and flow moves to the step S230 in FIG. 2. When all N segments have not yet been processed in the step S222, the step S223 measures the photoacoustic signal 110 generated from the target area 108 with the ultrasonic transducer 104. A measured signal value is stored in the memory in the control apparatus 105 with a phase value $\Phi_j$ of the segment j. For example, assume that j is 1. Then, the photoacoustic signal 108 is measured when the phase distribution set in the step S260 (or the wavefront optimized at the depth $z_{i-1}$ in the last procedure) or the plane wave at the position $z_0$ is irradiated onto the medium.

Next, the steps S224 to S225 gradually increase or increment a value of a phase modulation amount ΔΦ (according to a discrete step size), provide the phase $\Phi_j$ of the segment j with the phase modulation amount ΔΦ, and update the phase value of the segment. The step S224 determines whether the phase modulation amount ΔΦ exceeds 2π, and when it does not exceed 2π, the step S225 sets the phase value $\Phi_j$ of the segment j to $\Phi_j+\Delta\Phi$ and updates the value of the phase $\Phi_j$ by adding the phase modulation amount ΔΦ. The step S223 again measures the photoacoustic signal generated from the target area 108 for the newly updated phase $\Phi_j$, and stores the measured data in the memory in the control apparatus 105. This procedure is repeated until the phase modulation amount ΔΦ of the segment j exceeds 2π.

When the phase modulation amount ΔΦ exceeds 2π and the measurement ends in the step S224, the optimal phase $\Phi_j$ is read out that maximizes the photoacoustic signal from the data stored in the memory in the step S226 and set to the phase of the segment j in the SLM 102. The step S227 moves to the next segment j+1 on the SLM 102, and executes the optimization in the steps S222 to S227. Thus, the optimization processing is executed for all segments on the SLM 102, and generates the incident light 106 to be focused on the set target area.

While this embodiment reads the phase $\Phi_j$ that maximizes the photoacoustic signal in the step S226, the phase may provide at least 75% of the maximum value of the photoacoustic signal, preferably 85% of the maximum value of the photoacoustic signal, and more preferably 95% of the maximum value of the photoacoustic signal.

Instead of the algorism for sequentially optimizing the phase of each segment on the SLM, the optimization of the incident wavefront in the step S220 may use a partitioning algorism for simultaneously optimizing a plurality of segments as disclosed in I. M. Vellekoop, A. P. Mosk, "Phase control algorithms for focusing light through turbid media," Optics Communications 281 (2008) pp. 3071-3080. Alternatively, the optimization may use a genetic algorithm as disclosed in Donald B. Conkey et al., "Genetic algorithm optimization for focusing through turbid media in noisy environments," Optics Express Vol. 20, No. 5 (2012). In particular, when the photoacoustic signal is feeble, the portioning algorithm for simultaneously optimizing a plurality of segments or the genetic algorithm is effective.

When the optimization processing in the step S220 ends, the flow moves to the process of S230 illustrated in FIG. 2. The step S230 determines whether the target position $z_i$ reaches the depth (target position) to measure the optical property in the medium using the photoacoustic signal. If it does not reach the depth, the flow moves to the step S240.

Figure 4:
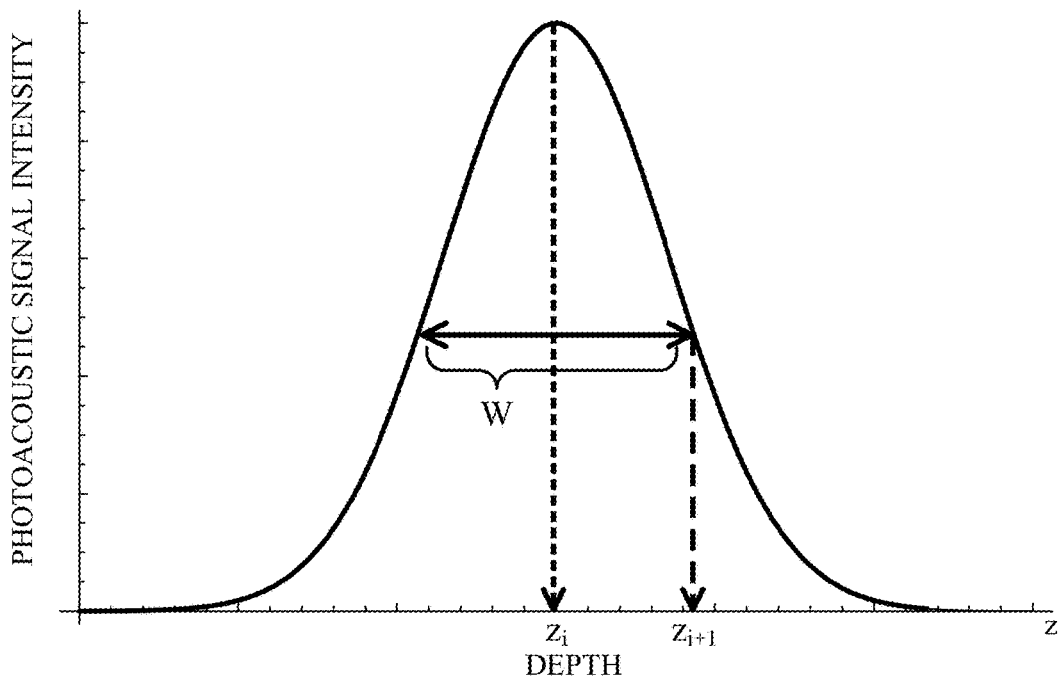
FIG. 4 illustrates a distribution in a depth (z) direction of a photoacoustic signal in a target area according to the first embodiment of the present invention.

FIG. 4 illustrates a profile of the photoacoustic signal in the depth direction (z direction) in the target area 108 when the optimized incident wavefront at the target position located at a certain depth $z_i$ is irradiated onto the medium 107. The optimization effect of the step S220 enhances the intensity of the photoacoustic signal in comparison with the normal light irradiation, and the signal intensity has a peak at the depth $z_i$ and has a shape that spreads in the depth direction (with full width at half maximum (FWHM) W) (and also spreads in in a sectional direction perpendicular to the depth direction). Therefore, the ultrasonic transducer 104 can measure the profile of the photoacoustic signal illustrated in FIG. 4. The step S240 measures the FWHM W of the signal distribution obtained by the optimization effect of S220, as illustrated in FIG. 4.

Next, the step S250 sets the target position $z_{i+1}$ used to optimize the wavefront in the iterating processing. The next target position $z_{i+1}$ changes based on the area that enhances the measurement signal when the light having the wavefront (first wavefront) optimized at the current target position $z_i$ is irradiated onto the medium. More specifically, as illustrated in FIG. 4, the target position (measurement position) is changed, as long as the value of the measurement signal that changes in the depth direction is larger than a threshold. For example, the target position is changed in a range larger than half of the maximum value of the measurement signal. As illustrated in FIG. 4, this embodiment sets the next target position as $z_{i+1}=z_i+W/2$ based on the measured FWHM W. The focus position of the ultrasonic transducer 104 may be changed in changing the target position, and the step S250 provides setting such that a focused position of the ultrasonic transducer 104 accords with the updated target position $z_{i+1}$.

One of the characteristics of the present invention is to update the target position as in the step S250 and to repeat this updating. When the optimization processing in the step S220 provides an optimization such that the photoacoustic signal is maximized at the position $z_i$, an area is formed in which the intensity of the photoacoustic signal enhances around the position. The spread of this area depends on the characteristic of the ultrasound focus volume set by the ultrasonic transducer 104, the correlation of the scattered wavefront when the shaped incident wavefront propagates to the target position, the number of independent optical modes that can exist, etc. In other words, the signal intensity of the photoacoustic signal enhances with a certain spatial spread due to both the characteristic peculiar to the medium and the controllable characteristic, such as an ultrasound focus volume. The present invention utilizes this effect in the optimization processing.

The step S260 maintains the setting of the wavefront (phase distribution) obtained by the optimization in the step S220 to the SLM 102 and returns to the optimization processing in the step S220. The optimization process in the step S220 sets the wavefront optimized at the position $z_i$ to the SLM 102 as the initial condition and starts optimizing the wavefront on the basis of this wavefront. When the wavefront optimized at this position $z_i$ is introduced into the medium 107, the signal intensity that is about half of the signal intensity obtained in the last procedure is obtained at the new target position $z_{i+1}$ as the initial condition of the optimization processing. The signal intensity has a significantly enhanced in comparison with the one obtained when the light having unshaped wavefront is introduced into the medium. Thus, the optimization processing in the step S220 can become efficient by utilizing the signal intensity as the initial condition. For example, a similar effect is disclosed in Thomas Bifano, Yang Lu, Christopher Stockbride, Aaron Berliner, John Moore, Richard Paxman, Santosh Tripanthi and Kimani Toussaint, "MEMS spatial light modulators for controlled optical transmission through nearly opaque materials," Proc. of SPIE, Vol. 8253 (2012). This reference shifts the wavefront as long as the scattering has a correlation (as long as the memory effect appears) for the incident wavefront optimized so as to focus the light transmitting through the scattering medium. According to this reference, the optimization sets the shifted wavefront to the initial value and can efficiently generate a focus spot behind the medium.

The present invention prevents a target signal (photoacoustic signal) at the depth in the next step from being embedded in the noise by utilizing the incident wavefront optimized at the depth in the last procedure in addition to the efficiency of the optimization. Moreover, the iterative processing according to the present invention enables a signal generated from a deep position in the medium to be measured, which would not otherwise be measured in the normal light irradiation, optimizes the wavefront, and measures the local optical property. Thus, the present invention can deepen the depth (penetration depth) for measuring the optical property in the medium. Prior art has difficulties in measuring the signal due to the signal attenuations caused by the scattering and absorption where the target is set to the deeper position in the scattering medium, and thus in optimizing the incident wavefront by utilizing the signal.

When the target position reaches the target depth to measure the optical property in the step S230, the flow moves to the step S270. The step S270 introduces the wavefront optimized in the step S220 into the medium, and measures the photoacoustic signal at the target position for the measurement of the optical property based on the expression (1). When the step S270 measures the photoacoustic signal on the section located at this depth, the optimization processing iterated in the depth direction may be applied in the lateral direction on the section. For example, the flow moves to the processing in the S270 at a predetermined depth and measures the photoelectric signal by setting the incident wavefront optimized in the step S220 to the initial condition and by shifting the measurement position for the photoacoustic signal (target position) in the lateral direction (sectional direction relative to the depth direction). The incident wavefront is again optimized at the shifted target position, and the photoacoustic signal is measured. The photoacoustic signal can be measured on the section by repeating this process and the measurement result can be imaged.

As described above, this embodiment initially forms a first wavefront through first optimization processing so that the photoacoustic signal has a high intensity, which is generated from a measurement position (first measurement position) that is distant from a surface of the medium in the depth direction by a comparatively short distance (first distance). Then, this embodiment changes the measurement position to a measurement position (second measurement position) that is distant from the surface of the medium in the depth direction by a comparatively long distance (second distance longer than the first distance) so as to reduce the distance between the measurement position and the target position. Moreover, this embodiment introduces the light having the first wavefront into the medium, and updates the first wavefront to a second wavefront through the second optimization processing so that the photoacoustic signal generated from the changed measurement position (second measurement position) has a high intensity. This embodiment repeats the above processing until the second measurement position reaches the target position. In other words, the iterative processing sets the second measurement position to a new first measurement position, and updates the second wavefront to a new first wavefront. Thus, the processing step according to the present invention includes a light focusing step of shaping a wavefront down to the target depth illustrated in the steps S200 to S260, and a measurement step for measuring the optical property using the optimized wavefront (or the imaging step).

In the step S270, the target position 108 may be scanned only in the ROI (region of interest) area (an area in which the photoacoustic signal is to be measured) in the medium, the photoacoustic signal may be measured, and the absorption coefficient distribution of the ROI area may be quantitatively imaged. The display unit 112 may display the captured image (absorption coefficient distribution image). The control unit 105 serves as a generator configured to generate the image based on the detected photoacoustic signal, and the display unit 112 serves to display the generated image. When the scattering medium 107 is a living tissue and the photoacoustic imaging is used for a diagnostic purpose, the display unit 112 may display another diagnostic result and measurement data superimposed on the absorption coefficient distribution image obtained by this embodiment. The ROI area used for the photoacoustic imaging may be set based on the diagnostic result. Alternatively, the ultrasonic transducer 104 may send the ultrasound, and the ROI image may be set from the reflected signal (echo image).

The above measurement and processing may be made with a plurality of arbitrary wavelengths, and the spectral characteristic in the medium may be measured. The metabolism information, such as an ingredient ratio among oxyhemoglobin, deoxyhemoglobin, and water, and a degree of an oxygen saturation, may be calculated and imaged with the spectral characteristic. A distribution of the metabolism information in the medium is three-dimensionally calculated for the ROI area, and the display unit may display a tomographic image.

In order to reach the depth for measuring the photoacoustic signal as quickly as possible in the step S230, the step S222 in the optimization processing of the S220 does not have to execute the processing for all segments. For example, the optimization processing is executed for selected segments. Thereafter, when the photoacoustic signal has a sufficiently enhanced to the noise at the depth position $z_{i+1}$ next to the position $z_i$ and can be measured, the optimization processing of the step S220 may end and the flow may move to the next step, even when there are some unprocessed segments in the optimization. Alternatively, the photoacoustic signal may be monitored in parallel both at the position $z_i$ and at the position $z_{i+1}$, and the SLM area may be divided into two (or two SLMs may be used). At this time, the result of the wavefront optimized by one SLM may be monitored and optimized by the other SLM, and the measurement depth may be sequentially deepened in parallel.

When the optimization is sequentially proceeded down to the depth direction, a certain threshold may be set to the focus volume and the step size may be determined based on the threshold, instead of determining the step size at the next depth based on the FWHM W.

Second Embodiment

Figure 5:
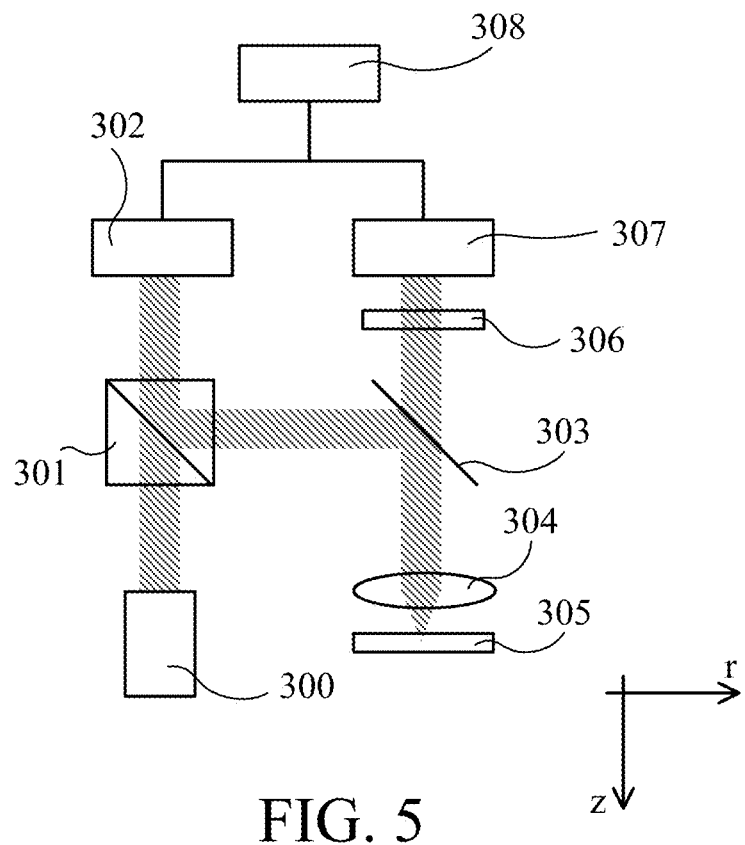
FIG. 5 schematically illustrates a configuration of a measurement apparatus according to a second embodiment of the present invention.

A description will be given of a measurement method and a measurement apparatus of the optical property in a scattering medium according to a second embodiment of the present invention. FIG. 5 schematically illustrates an exemplary configuration of the measurement apparatus according to this embodiment. A medium 305 is a test medium that contains a living tissue, and a scattering medium for light in the visible range to the near-infrared range. A description will now be given of an apparatus according to the present invention configured to measure and image a fluorescent signal generated from the medium 305.

A light source 300 radiates light having a wavelength, pulsed width, etc. adjusted based on a characteristic of the fluorescent material in the medium 305, etc. The light radiated from the light source 300 transmits a beam splitter 301 and is irradiated onto an SLM 302. A control unit 308 controls the SLM 302, and shapes (phase-modulates) the wavefront entering the medium 305 based on the optimization processing, which will be described later. The SLM 302 and the control unit 308 constitute a controller configured to control the wavefront of the light based on the output of a CCD, which will be described later. The light having a wavefront reflected on and shaped by the SLM 302 is reflected on the beam splitter 301, on a dichroic mirror 303, and enters the medium 305 via an optical system 304.

The light incident on the scattering medium 305 propagates to the focus volume set in the optical system 304 while being scattered inside the medium 305. The medium 305 contains a material that is excited by the light radiated from the light source 300 and emits fluorescent light. The light is focused on the focus volume by the optical system 304, the fluorescent material is excited around the focus volume, and the fluorescent signal is generated. The fluorescent signal is collected by the optical system 304, and the light having an excitation wavelength that becomes noise is filtered out through the dichroic mirror 303, and the fluorescent signal transmits. A band-pass filter 306 configured to selectively transmit a signal having a fluorescent wavelength enables the filtered fluorescent signal to enter a CCD 307. The CCD 307 serves as a detector (measurement unit) configured to detect (measure) the signal generated from the medium onto which the light is irradiated. Instead of the CCD 307, a CMOS sensor or an area sensor having an image intensifier or an EMCCD may be applied.

This fluorescent imaging apparatus shapes the wavefront of the incident light so as to enhance the intensity of the fluorescent signal generated from the local positon (target position) determined by the focus position in the optical system 304, similarly to the first embodiment. While monitoring the fluorescent signal measured by the CCD 307, the control unit 308 controls the SLM 302 so as to optimize the wavefront of the light incident upon the medium 305. Similar to the first embodiment, this embodiment also gradually deepens the target position to measure the fluorescent signal and sequentially optimizes the incident wavefront according to the target position. This processing enables the light to be efficiently focused on the deeper position in the medium and provides the fluorescent signal imaging. The processing flow according to this embodiment is similar to that of the first embodiment with reference to FIGS. 2 and 3 (although the photoacoustic signal in FIGS. 2 and 3 are replaced with the fluorescent signal). Referring now to FIGS. 2 and 3, a description will be given of the processing flow.

The initial target position $z_0$ corresponding to the step S200 in FIG. 2 is set to a sufficiently measurable depth that prevents the fluorescent signal from being embedding into the noise by properly adjusting the focus position in the optical system 304. The light source 300 is turned on in the step S210, and the flow moves to the optimization processing in the step S220 after the measurement of the fluorescent signal starts. The optimization processing in the step S220 is similar to that illustrated in FIG. 3. This embodiment may also use the partitioning algorism or the genetic algorism, instead of the optimization algorism illustrated in FIG. 3. This optimization can generate the incident wavefront that maximizes the intensity of the fluorescent signal at the target position.

This embodiment also determines the next target position $z_{i+1}$ in the depth direction according to the area in which the fluorescent signal enhances due to the optimization (the steps S240 and S250) and sets the incident wavefront optimized at the position $z_i$ to the initial condition of the optimization at the next position $z_{i+1}$ (the step S260).

Figure 6:
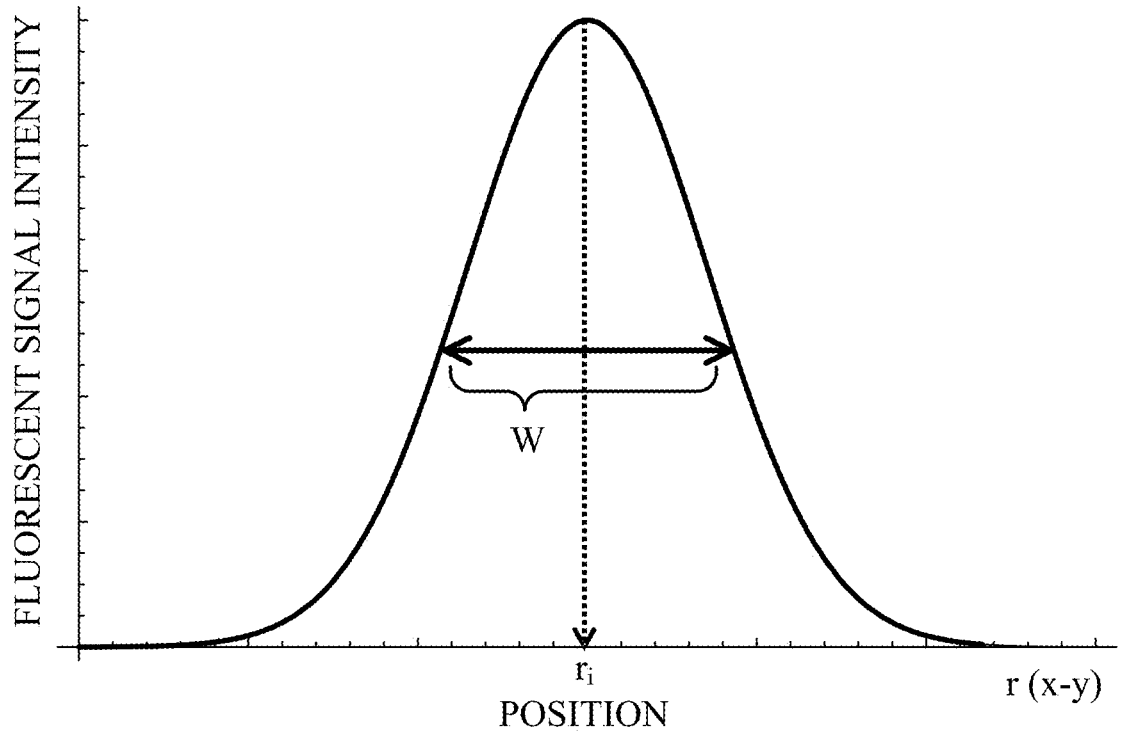
FIG. 6 illustrates a distribution in a lateral (XY section) direction of a fluorescent signal in a target area according to the second embodiment of the present invention.

FIG. 6 schematically illustrate a sectional profile of the fluorescent signal measured by the CCD 307 when the optimized incident wavefront enters the medium 305. The abscissa axis in the plot in FIG. 6 represents a position in the lateral direction r (x-y direction) perpendicular to the depth z direction in the medium, and the ordinate axis represents the intensity of the measured fluorescent signal. Herein, $r_i$ represents a center position on the x-y section in the target area and is located at the depth $z_i$. The step S220 optimizes the fluorescent signal generated from the center position and set to the target. In comparison with the light obtained by the normal light radiation, the intensity of the measured fluorescent signal enhances as a result of the optimization. As illustrated in FIG. 6, the intensity of the fluorescent signal spatially spreads around the target position and enhances. The intensity enhanced area depends on a focus spot diameter determined by the numerical aperture ("NA") of the optical system 304, and a correlation of the scattering wavefront when the shaped incident wavefront propagates to the position $r_i$.

Since this embodiment measures the fluorescent signal on the section corresponding to the focus position $z_i$ in the optical system 304 through the CCD 307, the spread of the fluorescent signal in the depth direction is not directly monitored unlike FIG. 4 according to the first embodiment. Thus, in order to obtain the profile in the depth direction in FIG. 4, the fluorescent signal may be monitored while the focus position $z_i$ of the optical system 304 is changed. The FWHM W of the distribution illustrated in FIG. 4 may be directly measured (in the step S240) based on the obtained profile, and the next depth $z_{i+1}$ may be properly set (in the step S250).

The next depth position $z_{i+1}$ may be set as follows based on the profile of the fluorescent signal in the lateral direction illustrated in FIG. 6. In general, the profile of the fluorescent signal having an intensity enhanced by the optimization extends in the depth z direction rather than the lateral direction r in an area (non-diffusion area) in which the light propagation is dominant in the depth z direction (forward direction) in the medium. As a result of the multiple scattering, in an area (diffusion area) in which the light propagation can be considered approximately isotropic, the above profile may be considered to approximately isotropically spread. Thus, in any cases, where W is the FWHM of the fluorescent signal, the signal intensity enhances at the next target position $z_{i+1}$ by the optimization result once the depth $z_{i+1}$ for the next target position is set to $z_{i+1}=z_i+W$ or to at least $z_{i+1}=z_i+W/2$. Hence, the next target position $z_{i+1}$ may be estimated and set based on the intensity distribution of the signal (fluorescent signal) on the plane perpendicular to the depth direction in the medium. The optimization is again repeated for the thus set depth $z_{i+1}$ by setting the wavefront optimized at the depth $z_i$ to the initial condition.

When the incident wavefront optimized at the depth $z_i$ in the last procedure is used to optimize the wavefront at the next procedure depth, the fluorescent signal of the target can be prevented from being embedded in the noise and the optimization of the wavefront can be efficiently converged. Moreover, the incident wavefront is sequentially optimized according to the target depth, the light is efficiently focused at the deeper position (in the light focusing step), and the medium is imaged with the fluorescent signal. For example, in an attempt at fluorescent imaging at a predetermined target depth, the steps S220 to S260 are repeated until the depth reaches the target depth. If it is unnecessary to measure the fluorescent signal at an intermediate depth, it is unnecessary to repeat the optimization of the step S220 until the convergence is reached. As long as the signal intensity enhances and is sufficiently measurable at the depth position in the next step, the optimization may be interrupted and the wavefront shaped at that time may be set to the initial condition for the next depth. Thereby, the processing can be accelerated and the target depth can be quickly reached for fluorescent imaging.

As described above, this embodiment initially forms a first wavefront so that the fluorescent signal has a high intensity, which is generated from a measurement position (first measurement position) that is distant from the surface of the medium in the depth direction by a comparatively short distance (first distance). Then, this embodiment changes the measurement position to a measurement position (second measurement position) that is distant from the surface of the medium in the depth direction by a comparatively long distance (second distance longer than the first distance) so as to approach to the target position, irradiates the light having the first wavefront onto the medium, and updates the first wavefront to a second wavefront so that the fluorescent signal generated from the changed measurement position (second measurement position) has a high intensity. This embodiment repeats the above processing until the second measurement position reaches the target position.

The iterative processing flow in the depth direction in the medium may be synchronized with the scanning flow for the fluorescent imaging. For example, profile data of the one-dimensional fluorescent signal in the depth direction is obtained in accordance with the processing flow illustrated in FIG. 2. The next data in the depth direction is similarly obtained by shifting the position to be imaged in the lateral direction (for example, by moving a stage configured to hold the medium 305). When this procedure is sequentially repeated for a certain ROI area in the medium 305, the fluorescent signal in this area can be three-dimensionally imaged. Moreover, the optimization may be efficiently executed for imaging at a new measurement position by setting the wavefront that has been optimized in the adjacent area to the initial condition in scanning in the depth direction or in the lateral direction. The unillustrated display unit may display the generated image.

Herein, the fluorescent signal contains a signal that is emitted by the multiphoton excitation in the nonlinear phenomenon as in the TPF. The present invention is not limited to imaging with the fluorescent signal. For example, the present invention is applicable to a method for measuring and imaging an ultrasound modulated light signal by irradiating light onto a medium as described in the following embodiment. The present invention is applicable to a method for measuring and imaging a second harmonic generation (SHG) and a third harmonic generation (THG) in the medium. The present invention is applicable to a method for imaging a signal caused by the Raman scattering that contains the stimulated Raman scattering (SRS), the coherent anti-Stokes Raman scattering (CARS), etc. The present invention is applicable to a method for sectioning, measuring, and imaging a signal generated from a specific depth in the scattering medium such as the optical coherence tomography (OTC) and a confocal microscope. Hence, the measurement signal according to the present invention may be, for example, any one of a photoacoustic signal, a fluorescent signal, an ultrasound modulated light signal, a harmonic signal, a Raman scattering signal, an OCT signal, and a light intensity signal obtained by a confocal optical system.

Third Embodiment

Figure 7:
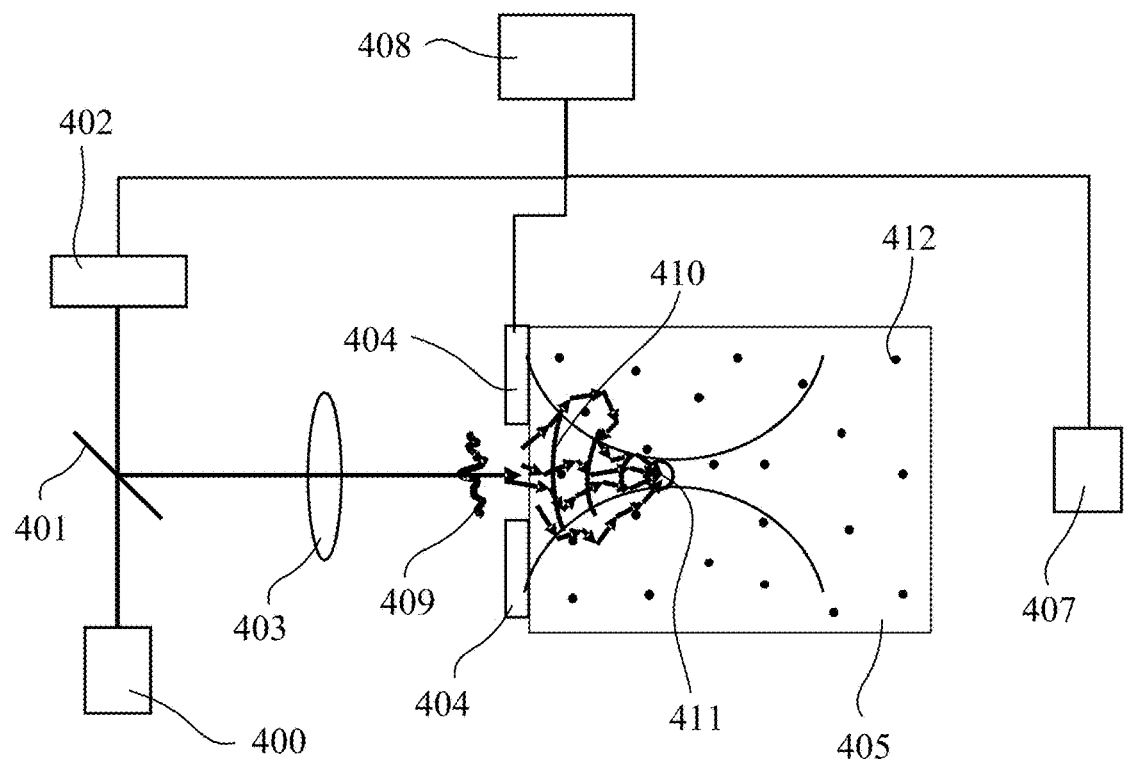
FIG. 7 schematically illustrates a configuration of a measurement apparatus according to a third embodiment of the present invention.

A description will be given of a measurement method and a measurement apparatus of the optical property of a scattering medium according to a third embodiment of the present invention. FIG. 7 schematically illustrates an exemplary configuration of the measurement apparatus according to this embodiment. A medium 405 is a test medium that contains a living tissue, and a scattering medium for light in the visible range to the near-infrared range. A description will now be given of an apparatus according to the present invention configured to irradiate an ultrasound onto the medium 405, to generate light modulated by the ultrasound (ultrasound modulated light), and to measure the optical property.

A light source 400 outputs pulsed light having a long coherence length, such as 1 m or longer, with dozens or hundreds of microseconds. The light emitted from the light source 400 has a wavelength selected among a plurality of wavelengths according to an absorption spectrum of an ingredient in the medium 405, such as water, fat, protein, oxyhemoglobin, and deoxyhemoglobin.

The pulsed light irradiated from the light source 400 transmits a beam splitter 401 and enters an SLM 402. A control unit 408 controls the SLM 402, and shapes (phase-modulates) the wavefront incident on the medium 405 based on the optimization processing, which will be described later. The SLM 402 and the control unit 408 constitute a controller configured to control the wavefront of the light based on an output of the detection system, which will be described later. Light 409 having a wavefront reflected on and shaped by the SLM 402 is reflected on the beam splitter 401, and enters the medium 405 via an optical system 403.

The ultrasonic transducer 404 introduces an ultrasound focused pulse 410 into the medium 405 and generates an ultrasound focus volume 411. The center of the ultrasonic transducer 404 has an opening through which the incident light 409 transmits, and the light and the ultrasound are coaxially irradiated onto the medium 405. The irradiated ultrasound has such a frequency in a range from 1 to dozens of MHz, and the control unit 408 properly adjusts the irradiated ultrasonic intensity. For example, when the medium 405 is a living tissue, the control unit 405 safely adjusts the ultrasonic intensity. The ultrasonic transducer 404 is sonically matched with the medium 405.

The light incident on the scattering medium 405 is multiply scattered and propagates inside the medium 405. Part of the multiple scattered light reaches the ultrasound focus volume 411. The refractive index of the medium is modulated by the ultrasound in the ultrasound focus volume 411, and a displacement of the scatterer (scattering particle 412) in the medium is induced by an ultrasonic frequency $f_a$. When the light enters the ultrasound focus volume 411, the light receives the phase modulation effect due to an optical path length change caused by the refractive index modulation and the displacement of the scattering particle, and the frequency shifts according to the ultrasonic frequency $f_a$. The light having a frequency shifted by the ultrasound (ultrasound modulated light) is irradiated from the ultrasound focus volume 411. The irradiated ultrasound modulated light again propagates inside the medium 405 while being scattered and is emitted from the medium 405.

In order to localize the ultrasound focus volume 411, the control unit 408 properly adjusts the irradiation timing of the ultrasonic pulse 410 and the incident light 409, and irradiates the incident light 409 at a timing when the ultrasonic focused pulse reaches the target position 411. A pulsed width of the ultrasound is set according to the size of the ultrasound focus volume 411 and the speed of the ultrasound in the medium.

A detection system 407 detects the ultrasound modulated light radiated from the medium 405. The detection system 407 serves as a detector or measurement unit configured to detect or measure the signal generated from the medium onto which the light is irradiated. The detection system 407 can include a single sensor, a lock-in amplifier, or a system that includes a bandpass filter and monitors the light intensity of the ultrasound modulated light having a shifted frequency. The single sensor may use a photo-diode (PD), an avalanche photo-diode (APD), a photomultiplier tube (PMT), etc. Alternatively, the single sensor may use a CCD, a CMOS, an EMCCD or another two-dimensional sensor array that combines the CCD with an image intensifier. The detection system 407 may use a system that measures a signal of a modulation depth relating to the signal intensity of the ultrasound modulated light based on the speckle contrast at each of turning-on and turning-off of the ultrasonic transducer 404 using the two-dimensional sensor array.

The optimization processing for shaping the wavefront of the incident light 409 is basically similar to that of illustrated in FIGS. 2 and 3. The control unit 408 controls the SLM 402 so as to maximize the ultrasound modulated light measured by the detection system 407, and shapes the incident wavefront similarly to FIG. 3. Since the ultrasound modulated light signal as an optimization target is a signal generated from the ultrasound focus volume 411, the optimized incident light is focused at the position (ultrasound focus volume 411) in which the ultrasonic focused pulse is localized. As described in the steps S240 to S260 in FIG. 2, where $z_i$ is a position at which the light is focused, the next target position $z_{i+1}$ is set based on the focus volume that spreads around the position $z_i$ and the optimization is performed at the updated position. The incident wavefront optimized at the position $z_i$ is set to the initial condition for the optimization at the next position $z_{i+1}$ and the optimization is iterated.

Figure 8:
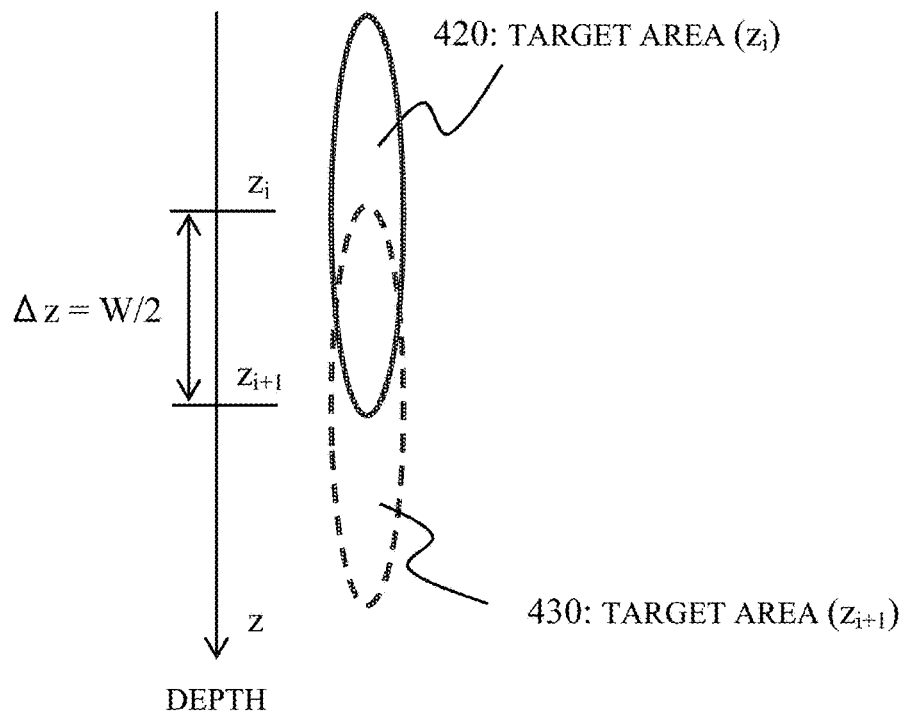
FIG. 8 schematically illustrates a target area (ultrasound focus volume) that spreads in a depth direction in a medium according to the third embodiment of the present invention.

The focus volume of the light obtained by the optimization of the incident wavefront can be controlled by the ultrasonic focusing parameters set by the ultrasonic transducer 404. FIG. 8 schematically illustrates localized positions (target areas) of the ultrasonic focused pulse in the medium 405. The ultrasound focus volume that extends in the depth direction (z direction) can be generated as illustrated in FIG. 8 by properly adjusting the pulse width of the ultrasonic pulse. When the length of the ultrasonic focus volume in the z direction is defined as the FWHM W of the ultrasonic focused pulse, W can be freely controlled by the pulse width of the electric signal applied to the ultrasonic transducer 404. Assume that the depth $z_i$ is the center position of the ultrasonic pulse, and the light is focused on the target area 420 in the optimization processing of the incident wavefront. As the processing corresponding to the steps S240 to S250 in FIG. 2, this embodiment sets the center position $z_{i+1}$ in the next target area 430 for the optimization to $z_{i+1}=z_i+W/2$ based on the pulse width W set by the control unit 408. This configuration can form the ultrasound focus volume in which the ultrasound is concentrated in the medium by introducing the ultrasound into the medium, and sets the next target position $z_{i+1}$ based on the length of the ultrasound focus volume in the depth direction. The incident wavefront optimized at the position $z_i$ is set to the initial condition for the optimization at the updated position $z_{i+1}$ and the optimization is again performed. The iterative processing sequentially optimizes the wavefront until the target depth is reached at which the optical property is to be measured.

One of the characteristics of this embodiment is to comparatively freely control the next step size $\Delta z$. As the pulse width of the ultrasound increases, $\Delta z$ becomes larger and the incident wavefront can be generated which can be efficiently focused at the target depth.

When the depth reaches the target depth (Yes in the step S230 in FIG. 2), the optical property in the medium is measured by setting the ultrasound modulated light to the measurement signal at the target depth. As described above, the localized optical property inside the medium 405 can be imaged by scanning the target area in the lateral direction on the section located at the same depth and by measuring the ultrasound modulated light. In the lateral scanning, the incident wavefront just previously optimized at the neighboring position may be set to the initial condition for the optimization of the incident wavefront at the next lateral position. For the lateral direction similar to the depth direction, an image may be captured by sequentially optimizing the incident wavefront. The ultrasound modulated light may be measured by spatially scanning the target area in the medium and the unillustrated display unit may display the captured image result.

As described above, this embodiment initially forms a first wavefront so that the ultrasound modulated light signal has a high intensity, which is generated from a measurement position (first measurement position) that is distant from the surface of the medium in the depth direction by a comparatively short distance (first distance). Then, this embodiment changes the measurement position to a measurement position (second measurement position) that is distant from the surface of the medium in the depth direction by a comparatively long distance (second distance longer than the first distance) so as to approach to the target position. This embodiment introduces the light having the first wavefront into the medium, and updates the first wavefront to a second wavefront so that the ultrasound modulated light signal generated from the changed measurement position (second measurement position) has a high intensity. This embodiment repeats the above processing until the second measurement position reaches the target position.

After the depth reaches the target depth in the light focusing step in the step S230, the optical property may be measured by changing the signal source to non-ultrasound modulated light. For example, the ultrasound modulated light is set to the optimization target signal and the light focusing step is executed down to the target depth. After the depth reaches the target depth, the fluorescent signal may be measured by utilizing the optimized incident wavefront. The light focusing step utilizing the ultrasound modulated light is executed with the light having a wavelength that excites the fluorescent material. The measurement step in the step S270 may switch to a light source for fluorescent imaging, of which output power is different but the same wavelength, if necessary. Hence, the light focusing step and the measurement step may use different measurement signals from each other. In the measurement step, the ultrasonic transducer 404 may be turned off. The measurement step may change the intensity of the incident light according to the measurement signal or switch the incident light to the super short pulsed light or continuous wave light (CW light) of which power is constant in time. The measurement signal in the measurement step can combine light for a variety of methods, such as the SHG light and Raman scattering light, other than the fluorescent signal, with the light focusing step. Thus, the signal detected from the target position may be different from a signal detected from a measurement position different from the target position.

Fourth Embodiment

Figure 9:
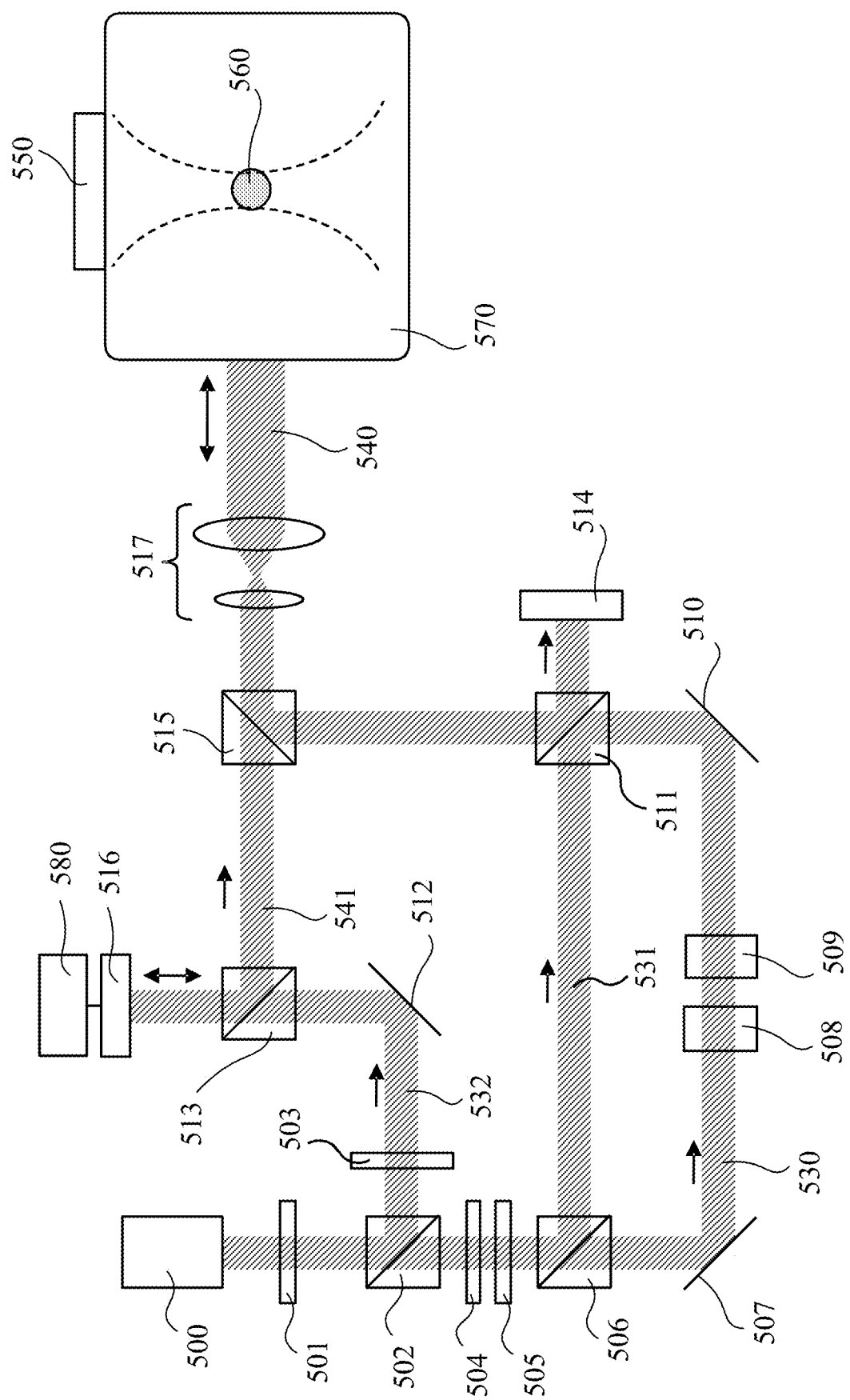
FIG. 9 schematically illustrates a configuration of a measurement apparatus according to a fourth embodiment of the present invention.

A description will be given of a measurement method and a measurement apparatus of the optical property in a scattering medium according to a fourth embodiment of the present invention. FIG. 9 schematically illustrates an exemplary configuration of the measurement apparatus according to this embodiment. Similar to the third embodiment, this embodiment is directed to the measurement apparatus utilizing the ultrasound modulated light.

Similar to the third embodiment, a light source 500 outputs pulsed light having a relatively long coherence length with dozens or hundreds of microseconds and a wavelength selected among a plurality of wavelengths according to an absorption spectrum of a contrast source to be measured in the irradiated medium, such as water and hemoglobin. The light is collimated and emitted from the light source 500, and its polarization direction is controlled by a half waveplate 501. Then, the light transmits a polarization beam splitter 502. At this time, a shutter 503 closes and a shutter 504 opens. The light that has transmitted the shutter 504 passes through a half waveplate 505 and a polarization beam splitter 506, and is divided into signal light 530 and reference light 531.

The signal light 530 is reflected on a mirror 507, and sent to Acousto-Optic Deflectors (AOMs) 508 and 509. The AOMs 508 and 509 are driven at individual frequencies, and adjusted so that a sum of their frequencies is equal to an ultrasonic frequency applied by an ultrasonic unit 550. For example, where the ultrasonic frequency $f_a$ is 2 MHz, the frequency of the AOM 508 is set to $f_1=-70$ MHz and the frequency of the AOM 509 is set to $f_2=+72$ MHz so that $f_1+f_2=f_a$ (=2 MHz).

An alternative for adjusting the frequency using the AOM is to arrange these two AOMs on the optical paths of the signal light and the reference light, and to adjust so that a frequency difference between them is the ultrasonic frequency $f_a$. For example, where the frequency of the AOM placed on the optical path for the signal light is $f_1$ (=70 MHz) and the ultrasonic frequency $f_a$ (=2 MHz), the frequency $f_2$ of the AOM placed on the optical path for the reference light may be set to $f_1+f_a$ (=72 MHz).

Signal light 530 having the frequency adjusted by the AOM passes the mirror 510 and the beam splitters 511 and 515, and is introduced into a medium 570 by an optical system 517. The medium 570 is a scattering medium that contains a living tissue.

The ultrasonic unit 550 contains an ultrasonic transducer, is acoustically matched with the medium 570, and focuses the ultrasound at a preset ROI area in the medium 570. The size of the formed ultrasound focus volume (target) 560 is set to a whole or part of the ROI area.

The ROI area in the medium 570 is an area in which a distribution of the optical property, such as the absorption and scattering, is to be measured and imaged. For example, when this embodiment is applied to a medical field, this ROI area may be set with a measurement result of the X-ray, MRI, ultrasonic echo image, etc. or another diagnosis result or prior information provided with another modality.

The irradiated ultrasonic frequency and the irradiated intensity are adjusted by an unillustrated control unit. The ultrasonic transducer included in the ultrasonic unit 550 includes, for example, a linear array probe, and generates the ultrasound focus volume 560 at an arbitrary position inside the medium 570 utilizing the electronic focusing with the array probe. The transducer can use a transducer utilizing a piezoelectric phenomenon, a transducer utilizing a light resonance, a transducer utilizing a capacity change, etc. As described above, the transducer irradiates a pulsed ultrasound so as to narrow the ultrasound focus volume 560 in the longitudinal direction (ultrasonic propagation direction). A pulse width of the ultrasound is set according to the size of the ultrasound focus volume 560 and the speed of the ultrasound in the medium, and the light source 500 irradiates the pulsed light in synchronization with a timing when the pulsed ultrasound reaches the target 560. The light source 500 may use the CW light instead of the pulsed light.

The light incident on the ultrasound focus volume 560 receives a modulation effect by the ultrasound, as described above, and the frequency shifts by $\pm f_a$ (primary component) according to the ultrasonic frequency. Thus, the frequency is adjusted for the incident signal light 530 so as to satisfy $f_1+f_2=f_a$ and the modulated light has a frequency shifted by $-f_a$ to the incident signal light 530 and equal to that of the reference light 531. The ultrasound modulated light having the shifted frequency is radiated from the ultrasound focus volume 560, again propagates inside the medium 570 while being scattered, and is emitted to the outside of the medium. Part of the ultrasound modulated light 540 is emitted to the light incident side and passes the opening in the optical system 517.

The ultrasound modulated light 540 having a frequency shifted by $\pm f_a$ that has been emitted from the medium 570 and transmitted through the optical system 517 and the scattered light (non-ultrasound modulated light) that has no shifted frequency are introduced to the CCD 514 via the beam splitters 515 and 511. The CCD 514 serves as a detector (measurement unit) configured to detect (measure) the signal generated from the light irradiated medium. The reference light 531 also enters the CCD. The optical path length of the reference light 531 may be properly adjusted so as to measure the reference signal, which will be described later.

The light that includes the ultrasound modulated light (light having the frequency shifted by $\pm f_a$) and the non-ultrasound modulated light and the reference light 531 interfere with each other on the CCD, and form interference fringes. Among the interference fringes, those formed by light fluxes having different frequencies (such as interference between the non-ultrasound modulated light and the reference light 531 and interference between the ultrasound modulated light having frequencies shifted by $+f_a$ and the reference light 531) have a beat frequency that vibrates at a speed equal to that of the ultrasonic frequency $f_a$ or higher. Usually, this frequency is very high and the interference signal is not recorded on the CCD. On the other hand, the CCD 514 measures the interference signal (digital hologram) between the ultrasound modulated light 540 and the reference signal 531 formed by the light fluxes having the same frequency $(-f_a)$.

An off-axis digital hologram is obtained by superimposing the ultrasound modulated light 540 on the reference light 531 with a fine angle less than one degree, for example, on the CCD (unillustrated). The off-axis digital hologram obtained by the CCD 514 is Fourier-transformed by an unillustrated signal processing unit and a spatial high-pass filter extracts and the interference term between the ultrasound modulated light 540 and the reference light 531. This is again Fourier-transformed and the amplitude and the phase of the ultrasound modulated light 540 are calculated. Instead of using the off-axis digital hologram, the phase distribution of the ultrasound modulated light 540 may be calculated by the phase shifting method. When the digital hologram signal is obtained by the CCD 514, the ultrasonic unit 550 may stop irradiating the ultrasound onto the medium 570.

A band-pass filter may be used to eliminate the non-frequency shifted light, to efficiently collect the frequency shifted light, and to form a hologram. For example, the Fabry-Perot interferometer or cryogenically-cooled spectral hole burning crystal may be used.

The phase distribution of the ultrasound modulated light 540 obtained by the CCD 514 is digitally inverted by the signal processing unit, and set on the SLM 516 with a pixel unit. The SLM 516 is controlled by the control unit 580, and forms the wavefront of the light that is to enter the medium. The SLM 516 and the control unit 580 constitute a controller configured to control the wavelength of the light based on the output of the CCD 514. For example, when the measured phase difference is $\Phi(x, y)$ on the CCD plane, the inverted phase set by the SLM is $-\Phi(x, y)$. At this time, the optical path length from the exit plane of the medium that emits the ultrasound modulated light 540 to the CCD 514 is set equal to that from the exit plane of the medium to the SLM 516. The CCD 514 and the SLM 516 are adjusted or corrected so that their phase distributions accord with each other with a pixel unit.

After the phase is set to the SLM 516, the shutter 504 closes and the shutter 503 opens. Light (reproduced light) 532 radiated from the light source 500 is reflected on the polarization beam splitter 502, and enters the SLM 516 via the mirror 512 and the beam splitter 513. The phase distribution set by the SLM 516 shapes the wavefront of the reproduced light 532, and converts the reproduced light 532 into a phase conjugate wave of the ultrasound modulated light 540, and enters the medium 570 as reproduced light 541.

The reproduced light 541 as the phase conjugate wave retrace its trajectory in the recording process of the digital hologram (or to measure the ultrasound modulated light 540), back to the target area 560 according to the time reversibility of the scattering. The light irradiation using the phase conjugate light enables the energy of the incident light to be highly efficiently sent to the target area 560 inside the medium 570. Instead of the digital hologram, this embodiment may employ hologram recording using a holographic material, such as a photo-refractive crystal.

According to the third embodiment, the reproduced light including the phase conjugate light of the ultrasound modulated light is substantially equivalent with the incident light when the ultrasound modulated light is optimized for the target in light focusing inside the light irradiated medium. This configuration has a light focusing effect around the target area (ultrasound focus volume) 560. While the wavefront shaping unit in this embodiment is different from that of the third embodiment (because the former uses the iterative optimization and the latter generates the phase conjugate light based on the wavefront measurement of the hologram), both can enhance the signal intensity of the ultrasound modulated light. Hence, this embodiment can also improve the depth (penetration depth) for the optical measurement by applying a flow similar to the processing flow according to the third embodiment after the reproduced light is irradiated onto the medium.

Figure 10:
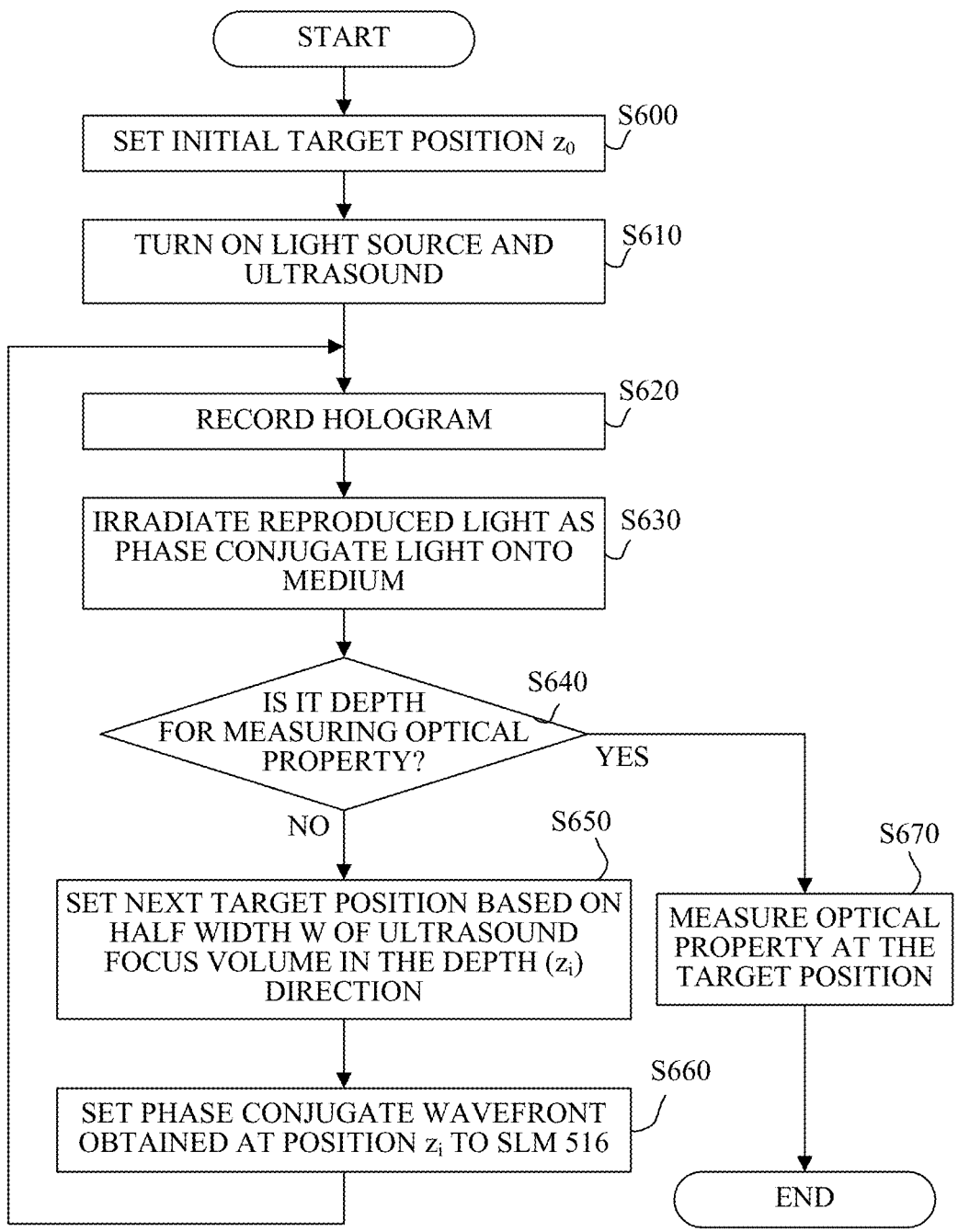
FIG. 10 schematically illustrates overall processing flow of a measurement method according to the fourth embodiment of the present invention.

Referring now to FIG. 10, a description will be given of a processing flow according to this embodiment. Initially, the step S600 sets the ultrasound focus volume 560 (at the target position $z_0$) as an initial condition. Assume that the depth of the target position $z_0$ (the depth from the surface of the medium based on the light incident position) is set where the ultrasound modulated light signal can be measured sufficiently. An appropriate depth at which the signal intensity can be measured may be searched after the measurement is repeated several times.

The step S610 turns on the light source 500, and the ultrasonic unit 550, and starts measuring the wavefront of the ultrasound modulated light (starts recording the hologram). As described above, in the step S620, the ultrasound modulated light 540 and the reference light 531 interfere with each other, and the CCD 514 obtains the digital hologram. The step S630 calculates the phase distribution of the ultrasound modulated light calculated based on the digital hologram, sets the phase distribution of the phase conjugate wave to the SLM 516, generates and introduces the phase conjugate light as reproduced light into the medium 570.

The step S640 determines whether the depth reaches the target depth at which the optical property of the target position is measured. Unless the depth reaches the target depth, the flow moves to the step S650.

The step S650 executes similar processing to that of the third embodiment. In other words, the next depth $z_{i+1}$ for the target area is set based on the current depth $z_i$ of the target area, and the ultrasonic unit 550 is controlled so as to generate the ultrasound focus volume at the depth $z_{i+1}$ position. As illustrated in FIG. 8, the ultrasonic pulse width is properly controlled and the next target position $z_{i+1}$ is set based on the FWHM W of the ultrasonic pulse. For the newly set target position $z_{i+1}$, the step S660 maintains the setting of the phase conjugate wavefront obtained by the hologram recording at the position $z_i$ to the SLM 516 and returns to the wavefront measurement in the step S620. The step S620 records the hologram of the ultrasound modulated light generated from the new target position $z_{i+1}$. The ultrasound modulated light generated from the ultrasound focus volume 560 at the position $z_{i+1}$ has a higher signal intensity than that of the normal incident light (such as a plane wave) irradiation by using the phase conjugate wavefront in the last procedure (at the position $z_i$) for the incident light in the wavefront measurement in the current procedure. Thus, the hologram of the ultrasound modulated light generated from the target position $z_{i+1}$ is recorded by utilizing an effect of enhancing the signal intensity. The iterative process from the step S620 to the step S660 (light focusing step) sequentially form a wavefront down to the target depth to be measured. This embodiment can also efficiently focus the light at the deep position in the medium, and measure the optical property by utilizing the signal enhancing effect with the spread of the properly set ultrasound focus volume 560 and by sequentially shaping the incident wavefront.

The step S640 ends the light focusing step. When the depth reaches the target depth (Yes in the step S640 in FIG. 10), this step sets the ultrasound modulated light at the target depth as the measurement signal and measures the optical property in the medium (measurement step). As described above, the optical property of the area can be imaged by scanning the ultrasound focus volume 560 in the depth direction or in the lateral direction on the same depth section and by measuring the ultrasound measured light. The unillustrated display unit can display the result of measuring and imaging the ultrasound modulated light by spatially scanning the ultrasound focus volume 560 in the medium.

As described above, this embodiment initially forms a first wavefront so that the ultrasound modulated light signal has a high intensity which is generated from a measurement position that is distant from the surface of the medium in the depth direction by a comparatively short distance (first distance). Then, this embodiment changes the measurement position to a measurement position (second measurement position) that is distant from the surface of the medium in the depth direction by a comparatively long distance (second distance longer than the first distance) so as to approach to the target position, irradiates the light having the first wavefront onto the medium, and updates the first wavefront to a second wavefront so that the ultrasound modulated light signal generated from the changed measurement position (second measurement position) has a high intensity. This embodiment repeats the above processing until the second measurement position reaches the target position.

As described above, after the light focusing step ends in the step S640, the imaging may be executed by changing the imaging signal source to a non-ultrasound modulated light. The optical property in the medium may be imaged by superimposing a plurality of signal sources on each other, for example, by combining the imaging using the non-ultrasound modulated light and the imaging using the ultrasound modulated light with each other.

Thus, the present invention properly shapes the wavefront of the light to be irradiated onto the medium (through optimization or using the phase conjugate wave), introduces the light into the medium and focuses the light at local area (target area) in the medium. As a result of the light focusing effect, the signal generated from the local area, such as a photoacoustic signal, a fluorescent signal, and an ultrasound modulated light signal, has an enhanced intensity. The present invention sets a next light focusing area utilizing the spread of the signal improving area in the depth direction at the local position, repeats this process, and sequentially shapes the incident light wavefront. Characteristically, this light focusing step efficiently sends the light down to the relatively deeper position in the scattering medium, and combines this process as an advance process with a variety of subsequent measuring and imaging methods. One of the characteristics of the present invention is to improve the penetration depth of measuring and imaging the optical property inside the medium.

The present invention can measure the optical properly in the scattering medium at a relatively deeper position.

Fifth Embodiment

Figure 11:
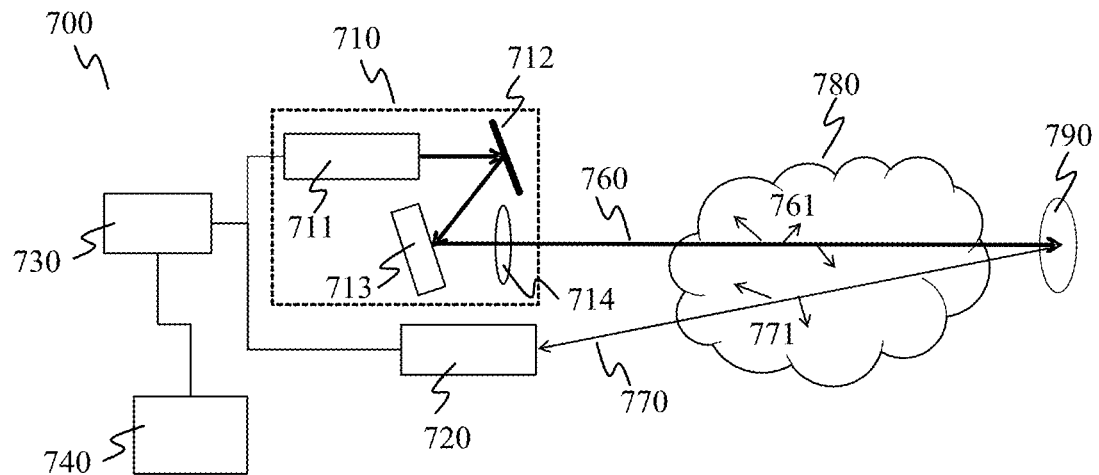
FIG. 11 schematically illustrates a configuration of a measurement apparatus according to a fifth embodiment of the present invention.

A description will be given of a measurement apparatus according to a fifth embodiment of the present invention. FIG. 11 schematically illustrates a configuration of the measurement apparatus according to this embodiment. A gate imaging apparatus 700 as a measurement apparatus according to the present invention includes a light source unit 710, a camera unit 720, a controller/processor 730, and a display unit 740, and is applicable, for example, to a camera configured to monitor a long-distance object. The gate imaging apparatus 700 captures an image of an object 790 across a scatterer 780 in the atmosphere. The scatterer 780 includes micro particles that float in the atmosphere, such as the mist, smoke, haze, smog, soil and dust of a micrometer size, snow, rain, and a fluctuation of a refractive index due to an uneven temperature distribution in the atmosphere. Under this condition, the gate imaging apparatus irradiates pulsed light onto the object, opens a shutter in the camera only at the instant when the pulsed light is reflected back from the object, and captures an object image by relatively reducing the scattered light.

The light source unit 710 mainly includes a laser light source 711 and an SLM 713. The laser light source 711 is generally referred to as an eye-safe laser, and emits infrared pulsed light with a wavelength from 1.4 to 1.8 μm band (short-wavelength infrared: SWIR). For example, the wavelength is 1.5 μm and the pulse width is one to dozens of nanoseconds, although another wavelength band and pulse width may be used according to the image capturing condition. The pulse repetition rate may be arbitrarily selected in a range from several Hz to hundreds of kHz, but may be generally high.

The laser light source 711 emits a collimated, pulsed light beam, which is in turn reflected on a mirror 712 and enters the SLM 713. The pulsed light is set so as to illuminate the effective area in the SLM 713. The SLM 713 may use, for example, the LCOS, DMD (digital mirror device), and transmission type liquid crystal. When the SLM 713 is a polarization dependent device, the polarization of the light incident on the SLM 713 is adjusted so that the its polarization direction accords with that of which the SLM 713 is functioning. A phase of the light incident on the SLM 713 is adjusted by the following process. The light reflected on the SLM 713 is emitted from the light source 710 after the optical system 714 adjusts the beam size and the polarization direction to desired ones. If necessary, a galvano mirror may be used to scan the pulsed light. The output intensity of a pulsed light beam 760 can be arbitrarily adjusted according to a condition, such as an object (whether it is a human or another living creature or a non-living creature) and an approximate distance to the object. For example, the output is within a range from dozens of mJ to hundreds of mJ.

The pulsed light beam 760 generates scattered light 761 when passing through the scatterers 780 in the atmosphere due to the influence of the scattering, and propagates to the object 790. The light reflected from the object 790 again passes through the scatterers 780 and propagates to the camera 720 with the scattered light 771. The object 790 is relatively distant, for example, by 100 m to dozens of kilometers. This embodiment uses infrared SWIR band light for the irradiated pulsed light, can decreases the scattered light in comparison with the visible light, and can safely illuminate the object with a stronger output than that of the visible light when the object 790 is a human. The above configuration is an advantage of a beam in the SWIR band.

The camera 720 includes a camera lens configured to sufficiently transmit light having a wavelength of 1.5 μm, and an array sensor sensitive to this wavelength. The focal length of the camera lens can be properly selected according to the distance to the object 790. As described above, a telephoto lens having a focal length of 1000 mm or longer may be used for the distant object 790. The array sensor can use an InGaAs sensor sensitive to that wavelength band. The shutter time period (gate time period) of the camera can be selected, for example, in a range from dozens of nanoseconds and several microseconds.

Image data captured by the camera 720 is transferred to the controller/processor 730. The controller/processor 730 controls the light source 710 and the camera 720 according to a measurement flow, which will be described later. The controller/processor 730 executes the wavefront shaping processing, which will be described later, irradiates the beam 760 having the wavefront shaped by the optimization processing onto the object 790, and acquires the gate image.

The captured image is displayed on the display unit 740. The display unit 740 may display an image captured in the middle of the measurement flow and an intermediate result of the wavefront shaping processing.

Figure 12:
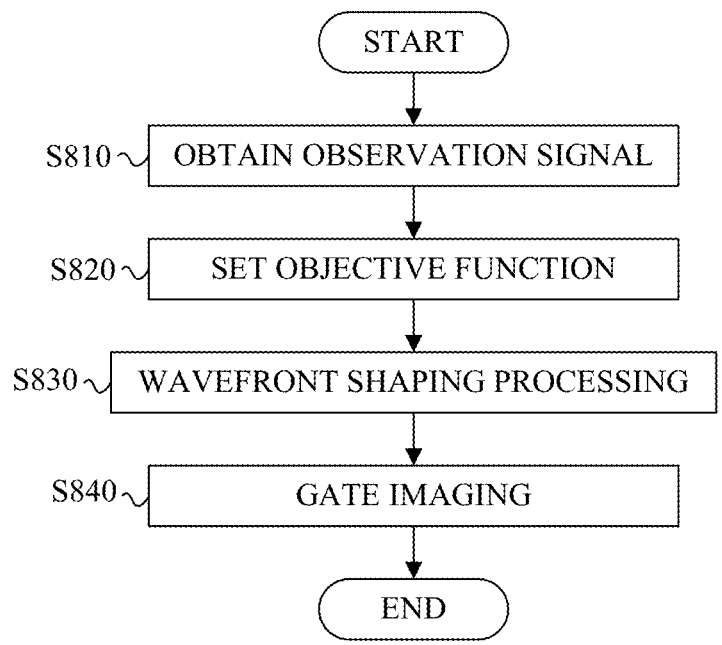
FIG. 12 schematically illustrates processing flow of a measurement method according to the fifth embodiment of the present invention.

FIG. 12 illustrates an illustrative measurement flow of the gate imaging apparatus 700 according to this embodiment. Initially, the step S810 irradiates the pulsed light beam 760 onto the object 790 and obtains the gate image. When a delay time period τ [sec] is set in the gate imaging, the gate imaging apparatus 700 captures the light reflected with an object distance L=τc/2[m]. Herein, c is a light speed in the atmosphere. When there is no object 790 in the object distance L, no significant signal regarding the object 790 can be observed. For example, when there is no object that reflects the pulsed light beam other than the scatterers 780 in the atmosphere in the object distance L, the captured image contains nothing other than a flare caused by the scattering. When there is another reflective object rather than the object 790 to be captured in the object distance L, the object other than the object 790 is captured. The step S810 sets the delay time period τ corresponding to the object distance L and provides the gate image, when the object distance of the object 790 to be captured is known in advance by another separate unit. At this time, for the whole or part of the image of the object 790, this embodiment may fine-adjust, before and after the delay time period τ, a delay time period that enables the highest signal intensity or highest contrast to be observed. Alternatively, when the object 790 is previously unclear, the gate imaging is performed by gradually changing the delay time period τ and once a meaningful signal is confirmed in the captured image, it may be set as the observation signal relating to the object 790, and the following flow may be executed. The present invention needs to obtain an observation signal (reflected light) relating to the object 790 in the gate image in the step S810. The observation signal may be a whole or part of an image of the object 790 distorted by the scattering and the fluctuation of the refractive index in the atmosphere.

Figure 13A:
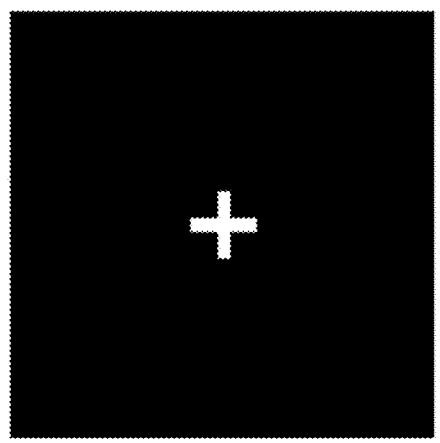
FIGS. 13A-13D simulate effects of the fifth embodiment of the present invention.
Figure 13B:
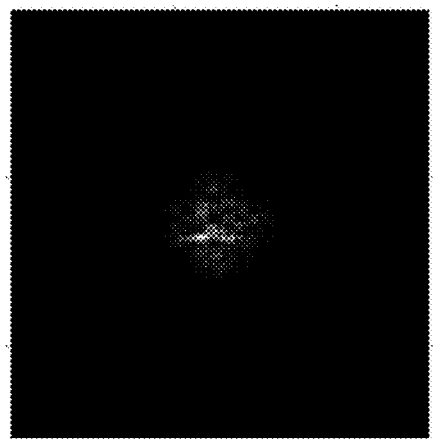

FIGS. 13A to 13D illustrate simulated results according to this embodiment. FIG. 13A illustrates an ideal image of the object 790 without any aberrations (deteriorations caused by the scattering). FIG. 13B illustrates an image obtained as a result of gate imaging in the step S810. The image in FIG. 13A is distorted by the scattering. Thus, the step S810 obtains the observation signal representing part of the image of the object 790. The observation signal setting condition may be that the luminance value of the image is higher than a predetermined threshold or a characteristic or feature shape can be confirmed. A characteristic shape may be extracted through the edge process or filtering process to the captured image. Alternatively, an observation signal may be determined based on a learning result of a characteristic amount of an image, such as an artificial object or a human, captured under a variety of scattering conditions.

Figure 13C:
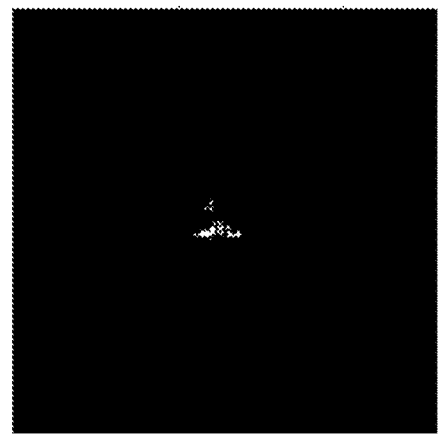

Next, the step S820 sets an objective function for the optimization of executing the wavefront shaping processing S830. This step utilizes the observation signal relating to the object 790 that has been obtained in the step S810. For example, a certain threshold is set to the observation signal (FIG. 13B) obtained in the step S810 and binary processing is executed so as to set a whole area extracted by the binary processing to a target area (FIG. 13C). The threshold may be determined based on the histogram of the luminance value of the captured image. The threshold is set as large as possible so as to prevent the target area from being excessively small. The binary processing can remove the noise component, such as the scattered light, obtained with the observation signal in the step S810. An average value or a sum of luminance values of pixels in the target area can be set to the objective function based on the image obtained by the gate imaging. Alternatively, a partial area having one arbitrary pixel or more in the target area may be set, and a sum of the luminance values in the partial area may be set to the objective function. A user may arbitrarily set the partial area as the ROI area. Even when the target area is divided into a plurality of areas in the captured image by the binary processing, the objective function may be set as described above. Alternatively, a separate target area in each divided area may be set individually as an objective function for the optimization, and the wavefront shaping in the step S830 may be performed with each objective function. The objective function may be set to a contrast value calculated based on luminance values in the target area and its neighboring area in the captured image after the target area is set. Thus, the step S820 sets the signal (such as a sum of the luminance values or contrast value) used for the objective function for the optimization based on the observation signal caused by the object measured in the step S810. When the wavefront shaping based on the optimization is applied to the gate image, it is necessary to clearly define the position and area of the objective function. The objective function may be determined by the user or automatically by the controller/processor 730 based on the result of the step S810. The target area and the objective function may be set based on prior information of the object 790, if any.

The step S830 shapes (optimizes) the wavefront of the pulsed light beam irradiated onto the object 790 so as to maximize the objective function value set in the step S820. The optimization processing shapes the wavefront of the pulsed light beam 760, irradiates the pulsed light beam 760 onto the object 790, and evaluates the value of the objective function through gate imaging. The wavefront shaping, the beam irradiation, the gate imaging, and the evaluation of the objective function are repeated and the wavefront is optimized so as to improve the value of the objective function. The wavefront shaping processing in the step S830 is performed similarly to that in FIG. 3 according to the first embodiment. FIG. 3 monitors the photoacoustic signal in the target area and sets the phase that maximizes the signal. On the other hand, this embodiment sets the phase that maximizes the value of the objective function set in the step S820. One of the characteristics of this embodiment is to specify the signal area (target area) derived from the object 790 based on the gate image, to set the objective function for the optimization based on the target area, and to shape the wavefront.

Figure 13D:
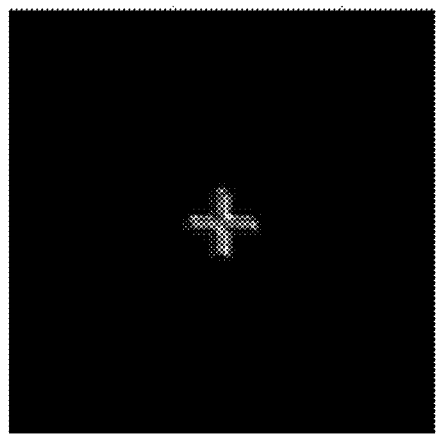

Next, the step S840 irradiates the pulsed light beam 760 optimized in the step S830 onto the object 790, and obtains the captured image through gate imaging (FIG. 13D). The processing in the step S830 can effectively irradiates the light onto the object 790, and capture the object image with a high SN ratio with the camera 720.

Figure 14:
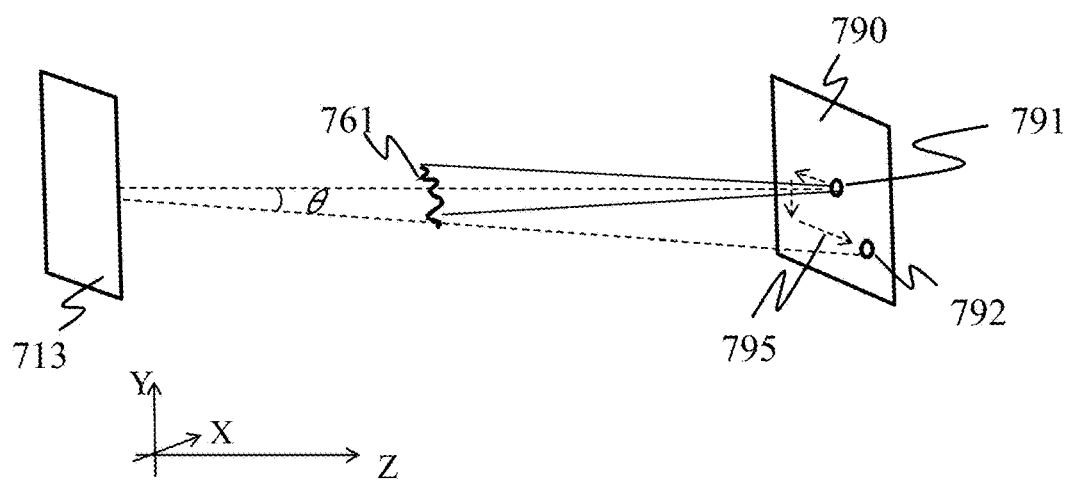
FIG. 14 schematically illustrates scanning of an irradiation beam according to the fifth embodiment of the present invention.

As illustrated in FIG. 14, after the step S840 is executed, gate imaging is performed for the target area 791 in the object 790 by scanning the irradiation angle of the pulsed light beam in the horizontal direction with the wavefront 761 obtained in the step S830. The horizontal direction is a horizontal direction (lateral direction X) on a plane perpendicular to the depth direction Z viewed from the gate imaging apparatus 700, in the atmosphere (medium) that contains the object. This configuration can obtain a captured image in a wide range (wide angle of view). An area range to be captured (target position and range) may be predetermined or determined based on the captured image. The scan amount 795 may be calculated, for example, by adding a linear phase shift amount according to the scan amount of the SLM 713 to the phase distribution obtained in the step S830. Alternatively, a separate scanning optical system may be used for scanning. This scanning is executed within a range that the correlation of the scattering is maintained. As long as the correlation of the scattering is maintained even when the incident angle is changed, the wavefront shaping effect can be maintained in the step S830. The vicinity of the target area may be imaged by utilizing this effect. The scanning range may be determined by monitoring the objective function set in the step S820 based on the capturing result with a variable incident angle. For example, the objective function may be larger than the initial value of the processing in the step S830.

When the luminance value of the image of the object 790 in the captured image lowers as a result of the scanning, the wavefront shaping processing is again executed. For example, a threshold of the objective function is determined and the scanning range is maximized so that it does not become equal to or lower than the threshold. In an attempt at scanning beyond this range, the wavefront shaping process in the step S830 is again executed by setting the wavefront shaped in the last step S830 to the initial value. At this time, the objective function may be reset by resetting the object 790 (S820). The gate imaging in the step S840 follows after the wavefront shaping processing is again performed. By iterating the wavefront shaping processing and the gate imaging, it is possible to realize a higher SN ratio and a wider angle of view in gate imaging. The wavefront shaping processing can maintain the effect of the previous wavefront shaping processing by utilizing the correlation of the scattering, and obtain the optimal, scanned incident wavefront quickly and efficiently. The threshold of the objective function is set, for example, to 50% or 30% as large as a value obtained in the step S830.

The pulsed light beam relative to the object 790 may be scanned in a perpendicular direction (longitudinal direction Y) on a plane perpendicular to the depth direction Z. Finally, images captured with respective angles of view are connected and the display unit 140 may display the resultant image.

As described above, this embodiment initially forms a first wavefront through first optimization processing so that the luminance signal of the object (objective function) has a high intensity (objective function) at a first measurement position that is distant from the object with a certain captured angle by a distance (first distance). Then, this embodiment controls the irradiation angle of the pulsed light beam and changes the measurement position to a measurement position (second measurement position) so as to approach to the target position (an image angle of view to be captured), irradiates the light having the first wavefront onto the medium, and updates the first wavefront to a second wavefront through the second optimization processing so that the luminance signal of the object generated from the changed measurement position (second measurement position) has a high intensity. This embodiment repeats the above process until the second measurement position reaches the target position.

The present invention covers supplying to a system or an apparatus that includes a computer, and executing a software program that enables the computer to implement a function of one of the above embodiments based on a recording medium directly or through wired/wireless communication.

In other words, the present invention covers a program code to be supplied and installed in the computer so as to implement the functional processing according to the present invention with the computer. The present invention covers a computer program that describes the procedure to implement the functional processing according to the present invention.

A type of the program language is not limited, such as an object code, a program implemented by the interpreter, and script data supplied to the OS, as long as it serves as the program. The storage medium that supplies the program may be, for example, a hard disk drive, a magnetic tape, or another magnetic recording medium, an optical/opto-magnetic recording medium, and a nonvolatile semiconductor memory.

The program may be supplied by storing the computer program according to the present invention in a server on a computer network, and by downloading the computer program with a connected client computer.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2016-133424, filed on Jul. 5, 2016, and 2017-113432, filed on Jun. 8, 2017, which are hereby incorporated by reference herein in their entirety.

What is claimed is:

1. A wavefront control apparatus comprising:
a detector configured to detect a signal generated from a medium onto which light is irradiated; and
a controller configured to control a wavefront of the light based on an output of the detector,
wherein the controller performs:
processing for forming a first wavefront of the light based on the signal generated from a first measurement position in the medium,
processing for setting a second measurement position in the medium different from the first measurement position in the medium based on the signal generated from the medium onto which the light having the first wavefront is irradiated, and
processing for forming a second wavefront of the light based on the signal generated from the second measurement position in the medium onto which the light having the first wavefront is irradiated.

2. The wavefront control apparatus according to claim 1, wherein the controller forms the first wavefront so that the signal has an intensity that is higher than 75% of a maximum value of the intensity of the signal generated from the first measurement position in the processing for forming the first wavefront, and forms the second wavefront so that the signal has an intensity that is higher than 75% of a maximum value of the intensity of the signal generated from the second measurement position in the processing for forming the second wavefront.

3. The wavefront control apparatus according to claim 1, wherein the controller sets the second measurement position to the first measurement position and the second wavefront to the first wavefront, and repeats the processing for forming the first wavefront and the processing for forming the second wavefront until the second measurement position reaches a target position.

4. The wavefront control apparatus according to claim 1, wherein the controller sets the second measurement position based on an area in which the signal has an intensity higher than a threshold when the light having the first wavefront is irradiated onto the medium.

5. The wavefront control apparatus according to claim 4, wherein the controller estimates the area based on an intensity distribution of the signal on a plane perpendicular to a depth direction in the medium.

6. The wavefront control apparatus according to claim 1, wherein the controller sets the second measurement position, based on an intensity of the signal that changes according to a position in a depth direction in the medium or in a direction perpendicular to the depth direction.

7. The wavefront control apparatus according to claim 1, wherein the controller sets the second measurement position as long as the intensity of the signal that changes according to a distance from a surface of the medium is larger than a threshold.

8. The wavefront control apparatus according to claim 6, wherein the threshold is half of a maximum value of the intensity of the signal.

9. The wavefront control apparatus according to claim 1, wherein the second measurement position is deeper than the first measurement position from a surface of the medium.

10. The wavefront control apparatus according to claim 1, wherein the controller irradiates an ultrasound onto the medium, forms an ultrasound focus volume on which the ultrasound is focused in the medium, and sets the second measurement position based on a size of the ultrasound focus volume in the depth direction in the medium.

11. The wavefront control apparatus according to claim 1, wherein the controller sets the second measurement position by controlling an irradiation angle of the light onto the medium.

12. The wavefront control apparatus according to claim 1, wherein the signal is one of a photoacoustic signal, a fluorescent signal, an ultrasound modulated light signal, a harmonic signal, a Raman scattering signal, an OCT signal, a light intensity signal obtained by a confocal optical system, or a luminance signal obtained by gate imaging.

13. The wavefront control apparatus according to claim 3, wherein the signal generated from the target position is different from the signal generated from a measurement position other than the target position.

14. An information acquiring apparatus configured to acquire information of an optical property inside a medium, the information acquiring apparatus comprising a wavefront control apparatus according to claim 1.

15. The information acquiring apparatus according to claim 14, further comprising:
  a generator configured to generate an image based on the signal detected by the detector; and
  a display unit configured to display the image generated by the generator.

16. A wavefront control method configured to control a wavefront of light to be irradiated onto a medium, comprising:
  forming a first wavefront of light based on a signal generated from a first measurement position in the medium;
  setting a second measurement position in the medium different from the first measurement position in the medium based on the signal generated from the medium onto which the light having the first wavefront is irradiated; and
  forming a second wavefront of the light based on a signal generated from the second measurement position in the medium onto which the light having the first wavefront is irradiated.

17. A non-transitory computer-readable storage medium storing a program that enables a computer to implement a wavefront control method configured to control a wavefront of light to be irradiated onto a medium,
  wherein the wavefront control method comprises:
  forming a first wavefront of light based on a signal generated from a first measurement position in the medium;
  setting a second measurement position in the medium different from the first measurement position in the medium based on the signal generated from the medium onto which the light having the first wavefront is irradiated; and
  forming a second wavefront of the light based on a signal generated from the second measurement position in the medium onto which the light having the first wavefront is irradiated.

* * * * *